US 11,779,277 B2

United States Patent
Athanasiou

(10) Patent No.: US 11,779,277 B2
(45) Date of Patent: Oct. 10, 2023

(54) SYSTEMS AND METHODS FOR ENDOVASCULAR DEVICE DETECTION AND APPOSITION MEASUREMENT

(71) Applicant: Canon U.S.A., Inc., Melville, NY (US)

(72) Inventor: Lampros Athanasiou, Medford, MA (US)

(73) Assignee: Canon U.S.A., Inc., Melville, NY (US)

( * ) Notice: Subject to any disclaimer, the term of this patent is extended or adjusted under 35 U.S.C. 154(b) by 116 days.

(21) Appl. No.: 17/345,797

(22) Filed: Jun. 11, 2021

(65) Prior Publication Data

US 2022/0395230 A1 Dec. 15, 2022

(51) Int. Cl.
*G06T 7/136* (2017.01)
*A61B 5/00* (2006.01)

(52) U.S. Cl.
CPC .......... *A61B 5/6862* (2013.01); *A61B 5/6876* (2013.01); *A61B 5/7264* (2013.01); *A61B 5/7425* (2013.01); *G06T 7/136* (2017.01); *G06T 2207/10028* (2013.01); *G06T 2207/10101* (2013.01); *G06T 2207/20081* (2013.01);
(Continued)

(58) Field of Classification Search
CPC .................................................. A61B 5/6862
See application file for complete search history.

(56) References Cited

U.S. PATENT DOCUMENTS

| | | |
|---|---|---|
| 7,801,343 B2 | 9/2010 | Unal et al. |
| 8,750,615 B2 | 6/2014 | Rollins et al. |
| 9,173,591 B2 | 11/2015 | Elbasiony et al. |

(Continued)

FOREIGN PATENT DOCUMENTS

| | | |
|---|---|---|
| JP | 2018519018 A | 7/2018 |
| JP | 2019088772 A | 6/2019 |

(Continued)

OTHER PUBLICATIONS

Ancong Wang et al.; "Automatic stent strut detection in intravascular optical coherence tomographic pullback runs"; Int J Cardiovasc Imaging, 2013; 29(1): 29-38. Published online May 23, 2012 (see https://link.springer.com/article/10.1007/s10554-012-0064-y).

(Continued)

*Primary Examiner* — Oneal R Mistry
(74) *Attorney, Agent, or Firm* — Canon U.S.A., Inc. IP Division

(57) ABSTRACT

Devices, systems, and methods for stent detection and apposition are disclosed. Embodiments obtain a plurality of images of intravascular image data of a vessel wall and an endovascular device, generate a signal that represents the plurality of images, identify one or more images that correspond to the endovascular device based on the signal that represents the plurality of images, generate a representation of a three-dimensional (3D) shape of the endovascular device based on the one or more images, determine an apposition value of the endovascular device relative to the vessel wall using a representation of a 3D shape of a lumen segment that corresponds to the endovascular device, the apposition value based on a volume difference between the 3D shape of the lumen segment and the 3D shape of the endovascular device, and present information indicating the apposition value.

20 Claims, 17 Drawing Sheets

(52) U.S. Cl.
CPC .............. *G06T 2207/30021* (2013.01); *G06T 2207/30101* (2013.01)

(56) References Cited

U.S. PATENT DOCUMENTS

| | | |
|---|---|---|
| 9,852,504 B2 | 12/2017 | Begin et al. |
| 9,996,921 B2 | 6/2018 | Ambwani et al. |
| 10,094,649 B2 | 10/2018 | Bagherinia |
| 10,109,058 B2 | 10/2018 | Ambwani et al. |
| 10,229,494 B2 | 3/2019 | Lu et al. |
| 10,335,039 B2 | 7/2019 | Xu |
| 10,338,795 B2 | 7/2019 | Gopinath et al. |
| 10,529,093 B2 | 1/2020 | Griffin et al. |
| 10,568,586 B2 | 2/2020 | Begin et al. |
| 10,621,748 B2 | 4/2020 | Kunio et al. |
| 10,674,985 B2 | 6/2020 | Kunio |
| 10,842,589 B2 | 11/2020 | Kunio |
| 2014/0257087 A1 | 9/2014 | Elbasiony et al. |
| 2016/0000341 A1* | 1/2016 | Rotman ............... A61B 5/0215 606/41 |
| 2017/0169566 A1 | 6/2017 | Lu et al. |
| 2019/0029623 A1 | 1/2019 | Kunio |
| 2020/0142575 A1 | 5/2020 | Gopinath et al. |
| 2020/0205750 A1 | 7/2020 | Begin et al. |
| 2021/0077037 A1 | 3/2021 | Kunio |
| 2021/0100616 A1* | 4/2021 | Roy ....................... A61B 34/10 |
| 2023/0008714 A1* | 1/2023 | Rajguru ............... A61B 5/1076 |

FOREIGN PATENT DOCUMENTS

| | | |
|---|---|---|
| WO | 2012126070 A1 | 9/2012 |
| WO | 2016187231 A1 | 11/2016 |
| WO | 2021055837 A1 | 3/2021 |

OTHER PUBLICATIONS

Ughi et al.; "Automatic segmentation of in-vivo intra coronary optical coherence tomography images to assess stent strut apposition and coverage"; Int J Cardiovasc Imaging, Feb. 2012; 28(2):229-241. Published online Feb. 24, 2011 (see https://link.springer.com/article/10.1007%2Fs10554-011-9824-3).

Bruining et al.; "Automated Three-Dimensional Detection of Intracoronary Stent Struts in Optical Coherence Tomography Images"; 2011 Computing in Cardiology, 2011, pp. 221-224. Sep. 2011.

Tsantis et al.; "Automatic vessel lumen segmentation and stent strut detection in intravascular optical coherence tomography"; Med Phys. Jan. 2012;39(1):503-513. Published Dec. 30, 2011 (see https://aapm.onlinelibrary.wiley.com/doi/abs/10.1118/1.3673067).

Gurmeric et al.; "A New 3-D Automated Computational Method to Evaluate In-Stent Neointimal Hyperplasia in In-Vivo Intravascular Optical Coherence Tomography Pullbacks"; MICCAI 2009, Part II, LNCS 5762, pp. 776-785; Sep. 2009.

Zhao Wang et al.; "3-D Stent Detection in Intravascular OCT Using a Bayesian Network and Graph Search"; IEEE Trans Med Imaging. Jul. 2015; 34(7): 1549-1561. Jul. 2015.

Lu et al.; "Automated stent coverage analysis in intravascular OCT (IVOCT) image vols. using a support vector machine and mesh growing"; Biomedical Optics Express Jun. 1, 2019; 10(6):2809-2828. Published online May 16, 2019 (see https://www.osapublishing.org/boe/Tulltext.cfm?uri=boe-10-6-2809&id=412678).

Yang et al.; "A novel automated lumen segmentation and classification algorithm for detection of irregular protrusion after stents deployment"; Int J Med Robotics Comput Assist Surg. 2020;16:e2033. Aug. 2019.

Guo et al.; "An Automatic Stent Detection for Intravascular Optical Coherence Tomographic"; 2020 39th Chinese Control Conference (CCC), 2020, pp. 2844-2849. Jul. 2020.

Sanchis-Gomar et al.; "Epidemiology of coronary heart disease and acute coronary syndrome"; Annals of Translational Medicine, 2016; 4(13):256. AME Publishing Company; Jul. 1, 2016.

Mori et al.; "Malapposition: is it a major cause of stent thrombosis?"; European Heart Journal, vol. 37, No. 15, Apr. 14, 2016, pp. 1217-1219. Published online Jan. 21, 2016 (see https://doi.org/10.1093/eurheartj/ehw006).

Cortes et al.; "Support-Vector Networks"; Machine Learning, vol. 20, No. 3, pp. 273-297. Mar. 1995.

Ng; "Automatic thresholding for defect detection"; Pattern Recognition Letters, vol. 27, No. 14, pp. 1644-1649. Oct. 15, 2006.

Otsu; "A Threshold Selection Method from Gray-Level Histograms"; IEEE Transactions on Systems, Man, and Cybernetics, vol. 9, No. 1, pp. 62-66. Jan. 1979.

Gutierrez-Chico et al.; "Delayed Coverage in Malapposed and Side-Branch Struts With Respect to Well-Apposed Struts in Drug-Eluting Stents: In Vivo Assessment With Optical Coherence Tomography"; Circulation, vol. 124, No. 5; Aug. 2, 2011; pp. 612-623.

* cited by examiner

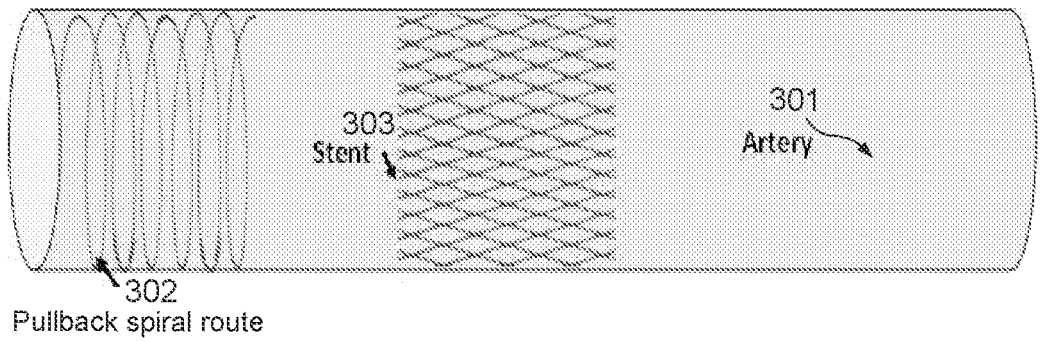
FIG. 3
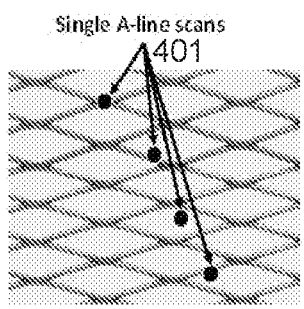
FIG. 4
Stent appearance in sequential A-line frames (500 scans)
 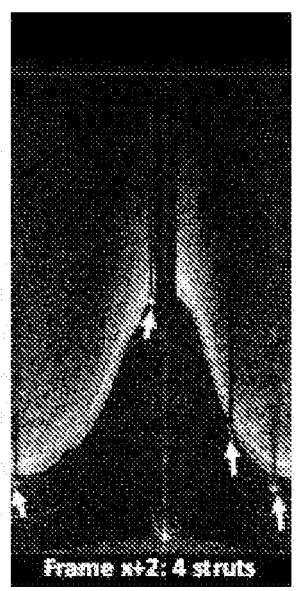 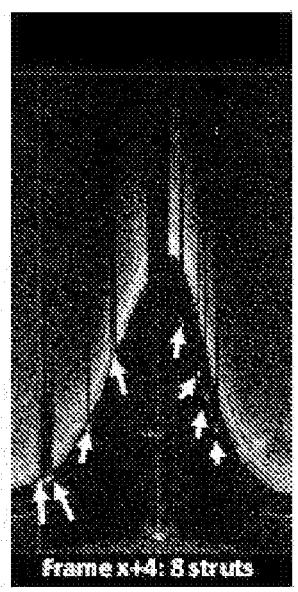
FIG. 5A    FIG. 5B    FIG. 5C

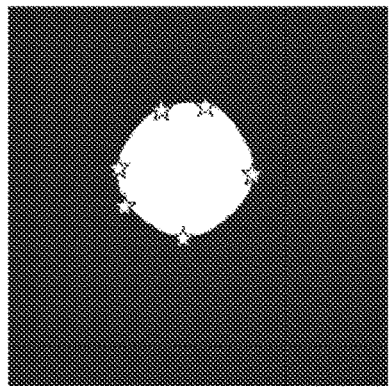
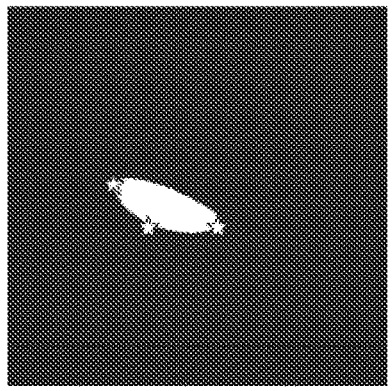
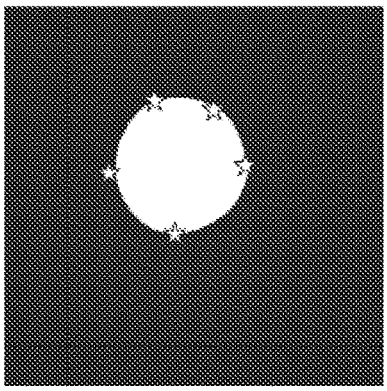
FIG. 22A    FIG. 22B    FIG. 22C
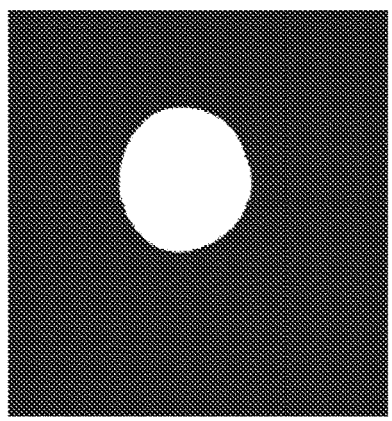
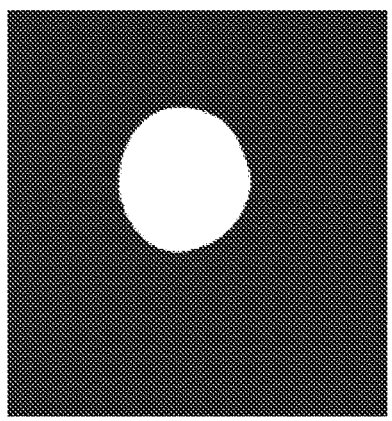
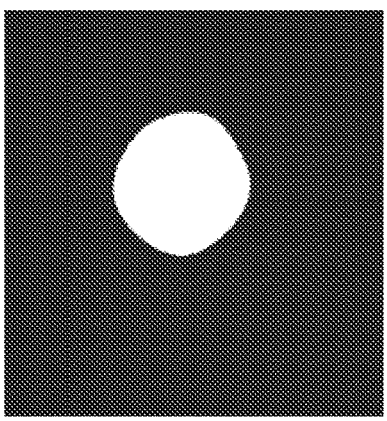
FIG. 23A    FIG. 23B    FIG. 23C

SYSTEMS AND METHODS FOR ENDOVASCULAR DEVICE DETECTION AND APPOSITION MEASUREMENT

TECHNICAL FIELD

The present disclosure relates to medical device detection and apposition, and more particularly to devices, systems, and methods for detecting an endovascular device, such as a stent, and measuring endovascular device apposition.

BACKGROUND

Coronary artery disease is a major cause of death in developed counties and is responsible for almost one third of all deaths in humans over 35 years old. The buildup of atherosclerotic plaques within the arterial wall leads to arterial stenosis which impairs the blood flow and finally leads to myocardial infarction.

A minimum invasive treatment of arterial stenosis includes the use of endovascular implants, known as stents, which aim at restoring the arterial geometry and increasing the blood flow supply to the myocardium. Stents are inserted into the stenosed vessel through a catheter and are expanded by inflating a balloon inside the stent, which simultaneously opens the stenosis and inflates the stent. After the balloon is deflated the stent remains inflated in the targeted area keeping it open. However, occasionally the stent is not fully apposed to the arterial wall creating serious future events. Stent apposition is examined visually using intravascular imaging modalities, such as optical coherence tomography (OCT), and is a procedure highly dependent on well-experienced readers. To overcome this limitation, automatic processing methods have been introduced in the literature. Some methods are able to detect the stent struts and perform stent apposition measurements. In conventional methods, however, the stent is not fully imaged in some intravascular images, and two-dimensional (2D) distance measurements are used to calculate a degree of apposition. Accordingly, conventional methods may be based on specific cross sections of the stent, since the stent is not fully imaged in all the intravascular images, and/or they may roughly estimate an apposition percentage based on 2D measurements.

SUMMARY

Systems, methods, and computer-readable media for detecting an endovascular device and measuring apposition of the endovascular device with respect to a vessel wall are disclosed.

According to some embodiments of the present disclosure, a system comprises one or more processors; and one or more computer-readable media storing executable instructions configured to be executed by the one or more processors, wherein the one or more computer-readable media and the one or more processors are configured to cause the system to: obtain intravascular image data of a vessel wall and an endovascular device, the intravascular image data comprising a plurality of images; generate a signal that represents the plurality of images; identify, in the plurality of images, one or more images that correspond to the endovascular device based on the signal that represents the plurality of images; generate a representation of a three-dimensional (3D) shape of the endovascular device based on the one or more images that correspond to the endovascular device; determine an apposition value of the endovascular device relative to the vessel wall using a representation of a 3D shape of a lumen segment that corresponds to the endovascular device, the apposition value based on a volume difference between the 3D shape of the lumen segment and the 3D shape of the endovascular device; and present information indicating the apposition value.

In some embodiments, images that each correspond to a respective cross section of an endovascular device, such as a stent, are identified and used to determine an apposition value indicating a percentage of the stent not fully apposed to a vessel wall. Embodiments of the present disclosure provide increased precision in apposition measurements by, for example, using all of the imaging cross sections of a stent, and by measuring stent apposition in 3D.

Further features of the present disclosure will become apparent from the following description of exemplary embodiments with reference to the attached drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the disclosure and, together with the description, serve to explain the principles of the disclosure.

FIG. 3 illustrates examples of a subject, stent, and spiral route of an imaging probe.

FIG. 4 illustrates positions of example A-line scans by an OCT imaging probe on the spiral route.

FIGS. 5A-5C illustrate example A-line images showing stent appearance in sequential frames of OCT image data.

FIG. 15A shows the carpet view image. FIG. 15B depicts bilateral filtering of the carpet view image of FIG. 15A. FIG. 15C illustrates an example binary image after bilateral filtering and binary segmentation of the carpet view image, and depicts a representation of a guidewire object.

FIG. 16 includes a vertical white line that corresponds to Frame X depicted in FIG. 17, and the vertical white line includes a gray segment (which bisects the white line) that corresponds to guidewire pixels depicted in FIG. 17.

FIG. 17 depicts a correspondence between the A-line image and guidewire pixels (depicted in FIG. 16 as a gray segment bisecting the vertical white line).

FIG. 18 (and corresponding FIGS. 19 and 20) depicts an example of stent strut detection.

FIGS. 22A-22C illustrate an example of three sequential binary frames each showing stent struts (stars) and a corresponding object (white) created using a spline over the stent struts.

FIGS. 23A-23C illustrate three sequential binary frames corresponding to the binary frames of FIGS. 22A-22C, respectively. FIG. 23B depicts an interpolation example.

DETAILED DESCRIPTION

Figure 1:
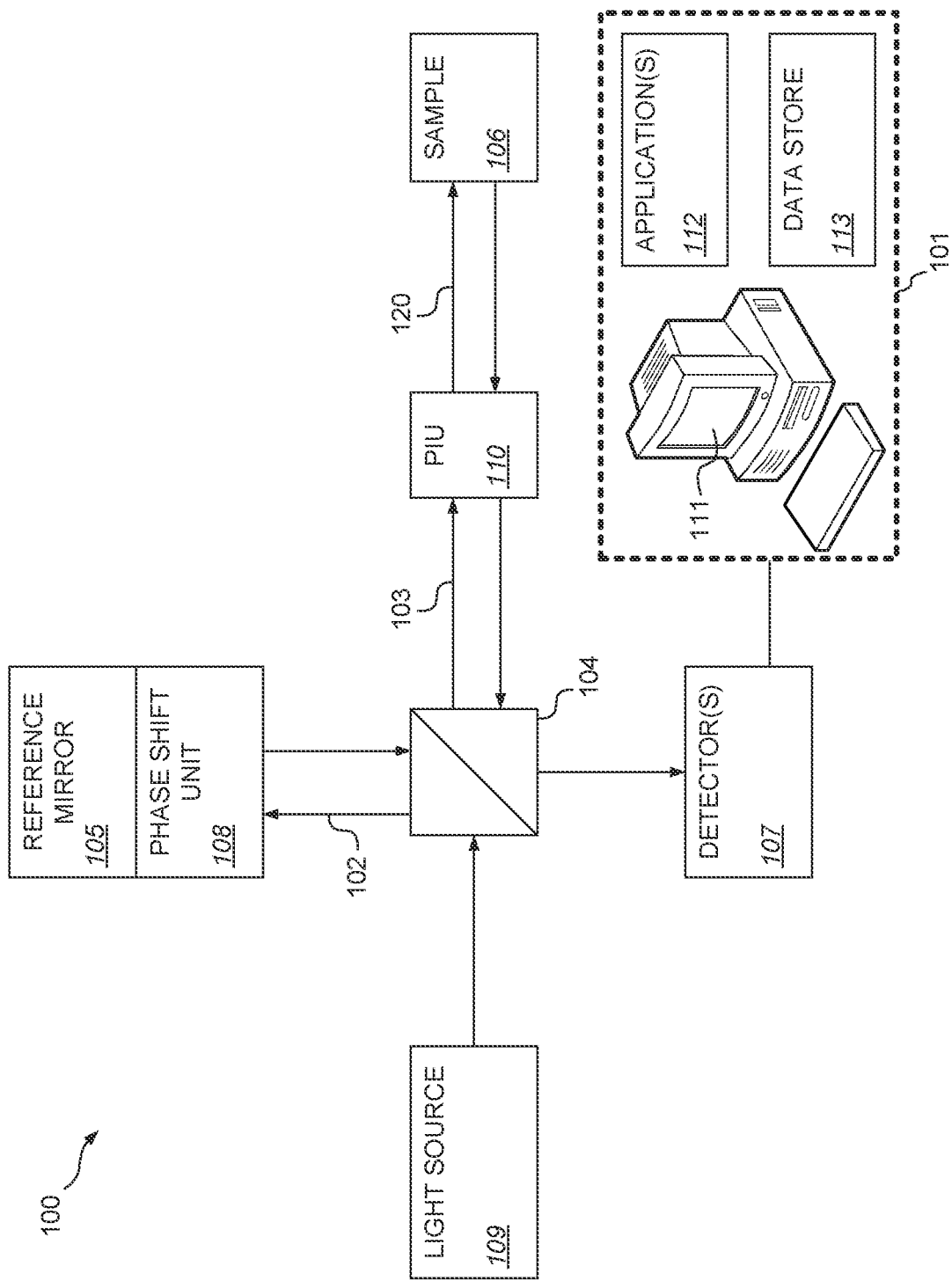
FIG. 1 illustrates an example Optical Coherence Tomography (OCT) system.

The following paragraphs describe certain explanatory embodiments. Other embodiments may include alternatives, equivalents, and modifications. Additionally, the explanatory embodiments may include several features, and a particular feature may not be essential to some embodiments of the devices, systems, and methods that are described herein. Furthermore, some embodiments include features from two or more of the following explanatory embodiments. Also, as used herein, the conjunction "or" generally refers to an inclusive "or," though "or" may refer to an exclusive "or" if expressly indicated or if the context indicates that the "or" must be an exclusive "or."

Improved systems and methods for detecting stents and for measuring stent apposition are disclosed herein. Features of the present disclosure provide improvements over current detection methods, including faster stent detection and increased accuracy of apposition percentage. For example, some embodiments include performing stent detection while reducing an amount of data processed, thereby reducing computational time required for stent detection. Moreover, features of the present disclosure provide for more accurate apposition measurements. For example, some embodiments include interpolating missing data along a surface of the stent, and using stent contours of each frame and corresponding lumen contours to generate three-dimensional (3D) volumes of the stent and lumen. The stent 3D volume is subtracted from the lumen 3D volume to obtain a volume difference between the respective 3D volumes, and the stent apposition percentage is determined based on the volume difference. Additional features and improvements of the present disclosure are described further below.

Intravascular imaging pullbacks result in a large number of two-dimensional (2D) images representing the arterial vessel. Stents are placed into a small part of the arterial vessel which represents ⅕-⅛ of the pullback images. Moreover, the number of stent struts shown in the stent frames are affected by the spiral movement of the imaging signal during the pullback; stent struts visible in each frame can vary from a small segment of the image representing the ⅛ of the cross section to the whole image representing the whole cross section. Currently available methods focus on scanning the whole arterial pullback, increasing the computational time, and on detecting all the individual stent struts seen in the 2D images. This leads to 2D distance measurements to calculate the degree of stent apposition which is a problem existing in the 3D space. Although some methods have been introduced which represent the stent in 3D, those methods do not allow for 3D measurements and are used for visualization purposes only.

Embodiments of the current disclosure overcome limitations of currently available methods identified above and provide fast and realistic stent apposition measurements. According to some embodiments, systems and methods disclosed herein perform one or more of the following: A) Import the pullback frames (2D A-line image frames) of an Optical Coherence Tomography (OCT) system, construct the carpet views of the pullback by averaging the A-lines of each image and extract the carpet view signal by averaging each vertical line of the carpet view image. B) Split the signal in 10-value segments, extract features for each segment and classify them to stent or not, indicating where the stent starts and ends in the carpet view. C) For each frame that corresponds to the stent create the A-line signal, by averaging each frame's A-line, and detect the A-line signal valleys. Each detected valley corresponds to a stent candidate A-line. D) Calculate the mean value of the frame's A-line signal and divide it by two to define the stent valley threshold (Thr). Then apply Otsu automatic thresholding to the carpet view image of step B, and define the guidewire object as the object that penetrates the carpet view. E) Detect the stent A-lines in each frame as the A-lines that correspond to valleys<Thr and do not belong to a guidewire object pixel. Then define as the stent strut the brightest pixel of each stent A-line. F) Average the missing/not detected struts of a frame using the pre and post frame struts and connect them using a spline. G) Use the lumen contours (for example, provided by an independent lumen detection algorithm) and translate each contour set (lumen and stent) in the 3D space. Create for each contour set a volume and calculate the stent apposition as their volume difference. The processes and features identified above are described in detail herein.

Turning now to the details of the figures, FIG. 1 shows an OCT system 100 which operates to utilize an OCT technique, including, but not limited to, one or more embodiments of stent, lumen, and/or artifacts detection techniques discussed herein, with optical probe applications in accordance with one or more aspects of the present disclosure. In some embodiments, the computing system 101 operates to control the OCT system 100. In some embodiments, the computing system 101 performs one or more steps of one or more methods described or illustrated herein. In some embodiments, the computing system 101 provides functionality described or illustrated herein. In some embodiments, software running on the computing system 101 performs one or more steps of one or more methods described or illustrated herein or provides functionality described or illustrated herein. Particular embodiments include one or more portions of the computing system 101. In some embodiments, the computing system 101 interacts with one or more entities of the OCT system 100 to control the OCT system 100. The computing system 101 may use any suitable protocol(s), standard(s), data exchange format(s), or combination(s) of these, to communicate with and send/receive information to/from one or more of the entities of the OCT system 100.

The computing system 101 includes application(s) 112 and a data store 113. These components of the computing system 101 reside in the computing system 101 in any suitable manner. For example, these components may reside on one or multiple devices. In some embodiments, one or both of these components may be provided as part(s) of a software application. In some embodiments, one or both of these components may be provided as a stand-alone software application.

The application(s) 112 include programs and related data. In some embodiments, the application(s) 112 executing on the computing system 101 perform one or more operations described or illustrated herein or provide functionality described or illustrated herein. For example, programs of the application(s) 112 may include instructions which, when executed by one or more processors, cause the computing system 101 to perform one or more operations described or illustrated herein. In some embodiments, the application(s) include data and one or more programs for performing stent detection and stent apposition measurement by executing the program instructions on the computing system 101 and performing one or more operations described herein. In some embodiments, the application(s) 112 executing on the computing system 101 interact with one or more entities of the OCT system 100. In some embodiments, the application(s) 112 executing on the computing system 101 may send requests to and receive information from one or more entities on a network. In some embodiments, the application(s) 112 executing on the computing system 101 present information on a display 111.

The computing system 101 provides functionality for maintaining and accessing information stored in the data store 113. In some embodiments, the application(s) 112 executing on the computing system 101 perform operations with respect to the data store 113. The computing system 101 may carry out various operations including, for example, adding entries to the data store 113; deleting entries from the data store 113; modifying entries in the data store 113; searching for entries in the data store 113; and retrieving entries from the data store 113. The information in the data store 113 may be organized in any suitable manner and may be organized for any suitable reason, such as for implementing the functionality of the application(s) 112. In some embodiments, the computing system 101 may perform one or more operations to add, delete, modify, search for, or retrieve one or more of the following in the data store 113: intravascular image data obtained from the OCT system 100, information generated using the intravascular image data, information related to a machine-learning model, or other suitable information. The intravascular image data may be, for example, image data of a blood vessel and a stent disposed within a lumen of the vessel, the intravascular image data including a plurality of images acquired by an OCT instrument, such as an optical probe, that emits and receives signals at a plurality of locations within the lumen of the vessel. The information generated using the intravascular image data may include, for example, a 2D representation of the intravascular image data in a carpet view, a signal generated from the carpet view image, information about features of the signal, a binary mask, contour objects, a representation of a 3D shape of a stent, a representation of a 3D shape of a lumen, information indicating a stent apposition value, or other suitable information.

The OCT system 100 includes a light source 109, a reference arm 102, a sample arm 103, a splitter 104, a reference mirror 105, and one or more detectors 107. The OCT system 100 may include a phase shift device or unit 108, and, in one or more embodiments, the phase shift device or unit may be omitted. In one or more embodiments, the OCT system 100 may include a patient interface device or unit (PIU) 110 and a catheter 120 (as diagrammatically shown in FIGS. 1-2), and the OCT system 100 may interact with a sample or target 106 (e.g., via the catheter 120 and/or the PIU 110). In one or more embodiments, the OCT system 100 includes an interferometer, or an interferometer is defined by one or more components of the OCT system 100, such as, but not limited to, at least the light source 109, the reference arm 102, the sample arm 103, the splitter 104 and the reference mirror 105.

The light source 109 operates to produce a light to the splitter 104, which splits the light from the light source 109 into a reference beam passing into the reference arm 102 and a sample beam passing into the sample arm 103. The splitter 104 is positioned or disposed at an angle to the reference mirror 105, the one or more detectors 107 and to the sample or target 106. The reference beam goes through the phase shift unit 108 (when included in a system, as shown in the OCT system 100), and the reference beam is reflected from the reference mirror 105 in the reference arm 102 while the sample beam is reflected or scattered from a sample 106 through the PIU (patient interface unit) 110 and the catheter 120 in the sample arm 103. Both of the reference and sample beams combine (or recombine) at the splitter 104 and generate interference patterns. The output of the OCT system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the OCT system 100 and/or the interferometer thereof are converted to digital signals to be analyzed with a computer, such as, but not limited to, the computing system 101. In one or more embodiments, the light source 109 may be a radiation source or a broadband light source that radiates in a broad band of wavelengths. In one or more embodiments, a Fourier analyzer including software and electronics may be used to convert the electrical analog signals into an optical spectrum.

The light source 109 may include a plurality of light sources or may be a single light source. The light source 109 generates broadband laser lights in one or more embodiments. The light source 109 may include one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 109 may be any light source that provides light which can then be split up into at least three bands in which each band is further dispersed to provide light which is then used to for spectral encoding of spatial information. The light source 109 may be fiber coupled or may be free space coupled to the other components of the OCT system 100.

In accordance with at least one aspect of the present disclosure, a feature of OCT systems is implemented using fiber optics. As aforementioned, one application of an OCT technique of the present disclosure is to use OCT with a catheter 120 as schematically shown in FIGS. 1-2.

Figure 2:
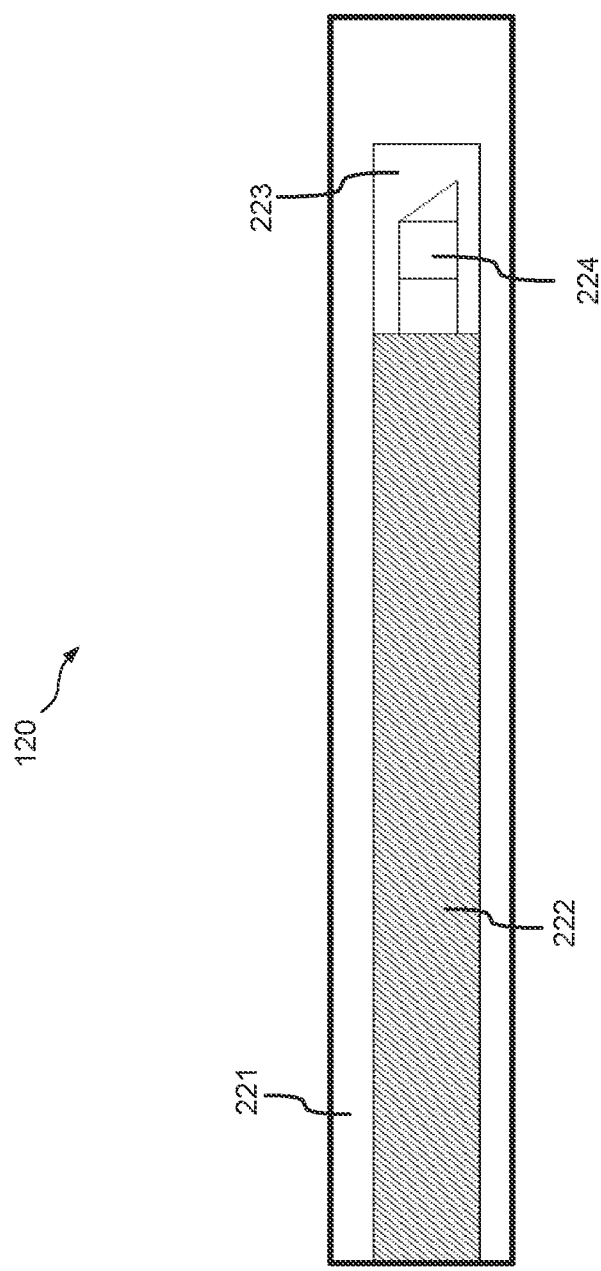
FIG. 2 illustrates an example catheter.

FIG. 2 shows an embodiment of the catheter 120 including a sheath 221, a coil 222, a protector 223 and an optical probe 224. As shown schematically in FIGS. 1-2, the catheter 120 preferably is connected to the PIU 110 to spin the coil 222 with pullback (e.g., at least one embodiment of the PIU 110 operates to spin the coil 222 with pullback). The coil 222 delivers torque from a proximal end to a distal end thereof (e.g., via or by a rotational motor in the PIU 110). In one or more embodiments, the coil 222 is fixed with/to the optical probe 224 so that a distal tip of the optical probe 224 also spins to see an omnidirectional view of a biological organ, sample, or material being evaluated, such as, but not limited to, hollow organs such as vessels, or a heart. For example, fiber optic catheters and endoscopes may reside in the sample arm (such as the sample arm 103 as shown in FIG. 1) of an OCT interferometer in order to provide access to internal organs, such as intravascular images, gastro-intestinal tract or any other narrow area, that are difficult to access. As the beam of light through the optical probe 224 inside of the catheter 120 or endoscope is rotated across the surface of interest, cross-sectional images of one or more samples are obtained. In order to acquire 3D data, the optical probe 224 is simultaneously translated longitudinally during the rotational spin resulting in a helical scanning pattern. This translation may be performed by pulling the tip of the probe 224 back towards the proximal end and therefore referred to as a pullback.

In one or more embodiments, the patient user interface 110 may comprise or include a connection component (or interface module), such as a rotary junction, to connect one or more components, such as one or more components of a probe (e.g., a catheter 120 (e.g., FIGS. 1-2)), a needle, a capsule, a patient interface unit (e.g., the patient interface unit 110), to one or more other components, such as, an optical component, a light source (e.g., the light source 109), a deflection section (e.g., such as the deflection or deflected section, which is a component that operates to deflect the light from the light source to the interference optical system, and then send light received from the interference optical system towards the at least one detector; a deflection or deflected section that includes at least one of: one or more interferometers, a circulator, a splitter, an isolator, a coupler, a fusion fiber coupler, a partially severed mirror with holes therein, and a partially severed mirror with a tap), the sample arm 102, a motor that operates to power the connection component and/or the patient user interface 110. For example, when the connection member or interface module is a rotary junction, preferably the rotary junction operates as discussed below). In one or more other embodiments, the rotary junction may be at least one of: a contact rotary junction, a lenseless rotary junction, a lens-based rotary junction, or other rotary junction known to those skilled in the art.

In at least one embodiment, the PIU 110 may include a Fiber Optic Rotary Junction (FORJ), a rotational motor and translation motorized stage (e.g., a portion of the PIU 110), and a catheter connector (e.g., a portion of the PIU 110). The FORJ allows uninterrupted transmission of an optical signal while rotating a fiber along the fiber axis. The FORJ may have a free space optical beam combiner including a rotor and stator.

In at least one embodiment, the computing system 101 operates to control motions of a motor and translation motorized stage, acquires intensity data from the at least one detector(s) 107, and displays the scanned image on the display 111 (e.g., a monitor, a screen). In one or more embodiments, the computing system 101 operates to change a speed of the motor and/or to stop the motor. The motor may be a stepping or a DC servo motor to control the speed and increase position accuracy.

In one or more embodiments, the computing system 101 operates to control the OCT system 100, the catheter 120 and/or one or more other above-described components of the OCT system 100. In at least one embodiment, the computing system 101 operates to acquire intensity data from the at least one detector 107 of the OCT system 100, and displays the image(s) on the display 111. The output of the one or more components of the OCT system 100 is acquired with the at least one detector 107 of the OCT system 100, such as, but not limited to, photodiodes, Photomultiplier tube(s) (PMTs), line scan camera(s), or multi-array camera(s). Electrical analog signals obtained from the output of the OCT system 100 or one or more components thereof are converted to digital signals to be analyzed with a computer, such as, but not limited to, the computing system 101. In one or more embodiments, the light source 109 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light.

In some embodiments, the computing system 101 includes the display 111, the display 111 being an integrated component of the computing system 101. In some embodiments, the display 111 and the computing system 101 are separate devices, the display 111 being an output device or an input/output device in communication with the computing system 101.

The computing system 101 communicates with the PIU 110, the catheter 120 and/or one or more other components of the OCT system 100 to perform imaging, and reconstructs an image from the acquired intensity data. The display 111 displays the reconstructed image, and may display other information about the imaging condition or about an object to be imaged. In some embodiments, the display 111 includes a liquid crystal display (LCD) and backlight which allow for output operations such as presenting information in a graphical user interface (GUI). In some embodiments, the display 111 includes a touch sensitive element operable to receive user inputs or commands based on the touching of interface elements presented in a GUI on the display 111. The interface element may be a graphical object displayed on the display 111. The display 111 also provides a GUI for a user to operate the OCT system 100, for example when performing OCT or other imaging technique, including, but not limited to, detection of stents, lumen edge(s), and/or artifact(s). An input may be provided using, e.g., a touch panel device, keyboard, mouse, or other input device connected to or included on the computing system 101. The computing system 101 instructs the OCT system 100 in accordance with one or more instructions based on the input(s) to set or change the imaging condition, and to start or end the imaging, and/or to start or end the lumen detection, stent(s) detection, and/or artifact(s) detection. The light source 109 of the OCT system 100 may have interfaces to communicate with the computing system 101 to send and receive the status information and the control signals.

In one or more embodiments, a search may be applied for each one-dimensional (1D) signal (e.g., A-line) of the image in polar coordinate for stent strut detection. In one or more embodiments of the present disclosure, an OCT image is formed in a polar coordinate system from A-lines. Each A-line includes information about the imaged object, such as, but not limited to: clear indications of artifacts from metal objects (e.g., stents, stent struts, guidewires) like narrow signal width and/or sharp rising and falling edges; significant difference in signal intensity and shape for unobstructed soft tissue compared to the sheath reflection and other artifacts like wide signal width and a gentle falling edge. Each A-line represents a cross-sectional 1D sampling of a target, sample, or object, such as, but not limited to, a vessel, along a certain view angle. As an imaging probe or device rotates (e.g., rotates about 0 to about 360 degrees, about 180 degrees to about 360 degrees, about 360 degrees), the corresponding A-lines form the complete two-dimensional cross-section of the target, sample, or object (e.g., vessel) in polar coordinates, which is converted into Cartesian coordinates to form the tomographical-view image of the cross-section of the target, sample, or object (e.g., vessel).

FIG. 3 illustrates an example of a subject (artery 301), a spiral route 302 of an imaging probe during a pullback, and a stent 303. The stent 303 is an endovascular implant placed into a stenosed vessel to keep it open and increase the amount of blood flow. The stent 303 may be a metallic circular mesh device. The OCT system 100 may be used to image the structure of the coronary arterial wall. The imaging probe may be an invasive optical catheter inserted into the coronaries through the femoral artery. The catheter performs a rotational spin during the pullback, and collects reflected optical signals, referred to as A-lines.

FIG. 4 illustrates positions of four separate A-line scans 401 by an OCT imaging probe on the spiral route 302 while the stent 303 is disposed within the artery 301, as shown in FIG. 3. In some embodiments, each group of A-lines represents a full spin of the catheter and corresponds to a respective cross section (2D OCT image frame) of the artery 301. Although four A-line scans 401 are depicted in the example shown in FIG. 4, an OCT application may include, for example, about 500 A-line scans for each frame corresponding to a cross section of the vessel. Any suitable number of A-line scans (such as, but not limited to, between 300 and 1,000 A-line scans) may be used for collecting data for each frame. Data collected from A-line scans 401 may be stored in one or more computer-readable media. In some embodiments, an imaging probe rotates and pulls back or pushes forward while scanning and recording images or video. In some embodiments, the collected data yields a three-dimensional dataset. In some embodiments, the collected data yields two-dimensional image frames (e.g., A-line images), where each frame provides a 360° slice of the vessel at different longitudinal locations. When the stented artery 301 is imaged, stent struts are present in a portion of the pullback images, appearing as bright formations followed by a shadow since light cannot penetrate their metallic structure. Due to the spiral movement of the catheter and the number of A-line light samples collected in each rotation to form the A-line image, some stent struts may not be visible in some OCT images. Stent appearance depends on the position of each of the A-line scans 401 and on the spiral route 302 the A-line scans 401 follow. Stent strut appearance variation in sequential frames of OCT images is depicted in FIGS. 5A-5C.

FIGS. 5A-5C illustrate stent appearance in sequential frames of OCT A-line images. In some embodiments, each A-line image in the respective frames of FIGS. 5A, 5B, and 5C is composed of respective data collected in about 500 A-line scans per frame. The A-line images in sequential frames show different numbers of stent struts. For example, in FIG. 5A, ten stent struts (identified by white arrows) are visible. On the other hand, in FIG. 5B, only four stent struts (identified by white arrows) are visible. And then in FIG. 5C, eight stent struts (identified by white arrows) are visible. This phenomenon reduces the number of stent struts that can be detected by some detection methods, which can also reduce the accuracy of stent apposition measurements that are based on 2D measurements of the visible struts. Embodiments of the present disclosure mitigate these issues.

In one or more embodiments, a position of a stent in intravascular image data of a pullback is automatically detected. In one or more embodiments, individual stent struts are automatically detected. In one or more embodiments, a percentage of stent apposition is automatically calculated.

Figure 6:
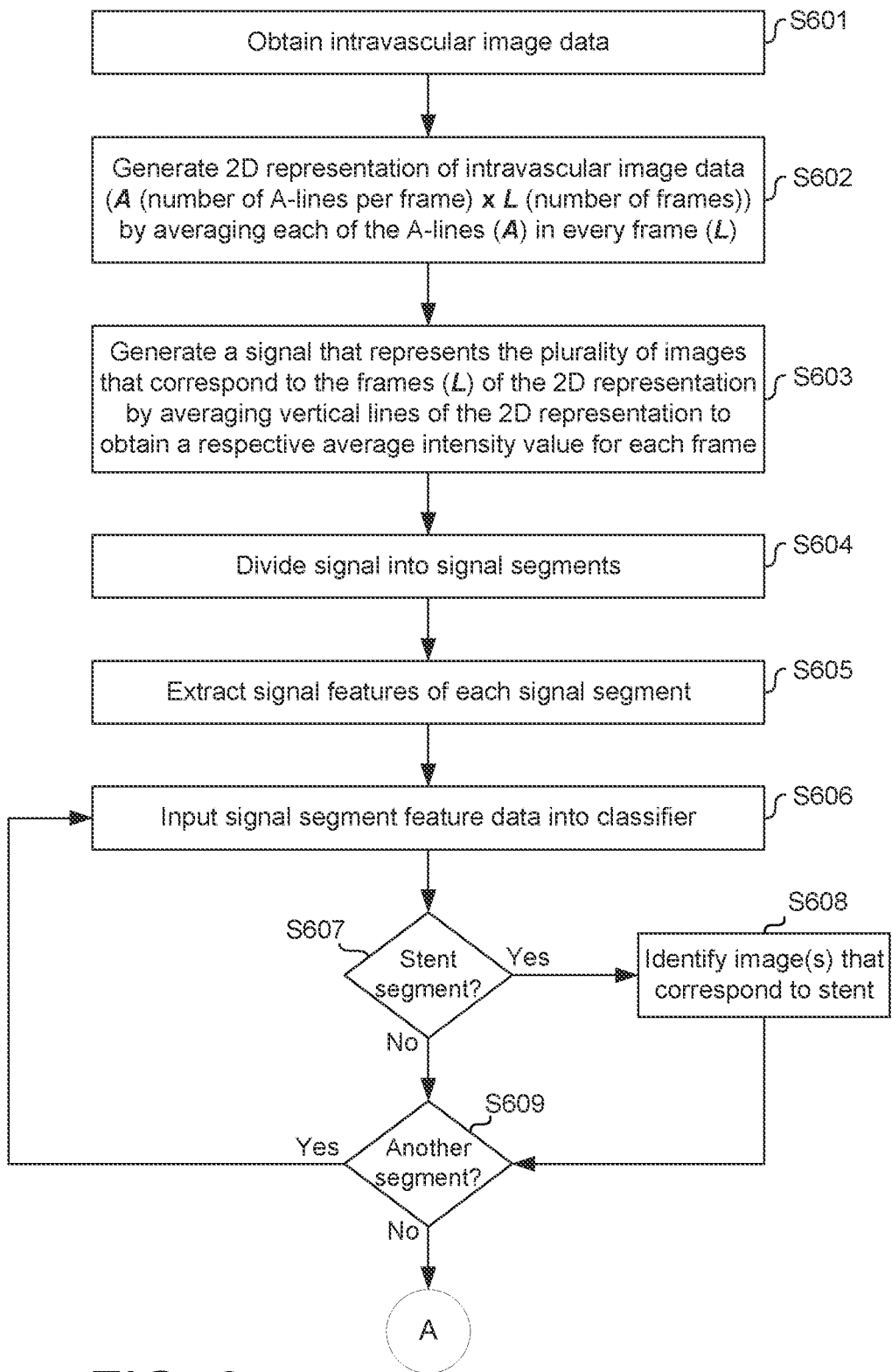
FIG. 6 illustrates an example operational flow for use in stent detection.

FIG. 6 illustrates an example operational flow for use in stent detection. In some embodiments, one or more of the steps of FIG. 6 are performed at the computing system 101 by executing program instructions of the application(s) 112 on the computing system 101.

In step S601, the computing system 101 obtains intravascular image data. In some embodiments, the computing system 101 obtains intravascular image data of a vessel wall and an endovascular device, such as a stent, disposed within a lumen of the vessel. The intravascular image data may include a plurality of images. For example, the intravascular image data may be a plurality of OCT image frames, each OCT image frame corresponding to a respective group of A-lines representing a full spin of the catheter inside the vessel. In some embodiments, each of the OCT image frames is a respective cross-sectional image of the vessel. In some embodiments, the plurality of OCT image frames includes one or more images that correspond to the endovascular device, where each of the one or more images corresponds to a respective cross section of the endovascular device. According to some embodiments, the intravascular image data comprises a plurality of A-line images.

The intravascular image data is obtained in any suitable manner in step S601. By way of example, and not by way of limitation, the intravascular image data may be obtained from one or more of the OCT system 100, one or more computer-readable media (e.g., memory or storage) on the computing system 101, remote storage, another source, or a combination of two or more of these. In some embodiments, the intravascular image data is obtained from the at least one detector(s) 107 of the OCT system 100. For example, the computing system 101 may acquire intensity data from the detector(s) 107. In some embodiments, all or a portion of the intravascular image data is included in the data store 113, and the computing system 101 obtains the intravascular image data by accessing the intravascular image data in the data store 113. For example, the computing system 101 may receive the intravascular image data from the OCT system 100, or other source, and store the intravascular image data in the data store 113; and, subsequently, the computing system 101 may retrieve the intravascular image data from the data store 113. In some embodiments, all or a portion of the intravascular image data is obtained via a network. For example, at least a portion of the intravascular image data may be received from a server computing system 2701, a client computing system 2702, another entity connected to a network 2703, or a combination of these, as discussed with reference to FIG. 27.

In step S602, the computing system 101 generates a 2D representation of intravascular image data having dimensions A×L, where A is the number of A-lines per frame and L is the number of frames. According to some embodiments, the 2D representation of intravascular image data is generated by averaging each of the A-lines (A) in every frame (L) of a pullback. For example, in some embodiments, the computing system 101 imports all the A-line images of the frames L (e.g., OCT image frames) obtained in a pullback, and averages each of the A-lines in every A-line image.

In some embodiments, the computing system 101 generates a carpet view image in step S602. For example, in step S602, the computing system 101 may generate a carpet view image using the intravascular image data obtained in step S601. According to some embodiments, a carpet view image is a 2D representation of a cross-sectional OCT image, but unrolled in a manner akin to unrolling a cylinder of carpet. The carpet view image is a representation of the A-lines by unfolding a cross-sectional or polar view along a longitudinal view. For example, the computing system 101 may generate the carpet view image by averaging each of the A-lines in every A-line image obtained from a pullback and displaying the average of each of the A-lines for every frame in two dimensions A×L (i.e., number of A-lines per frame by number of frames). An example of a carpet view image is depicted in FIG. 7.

Figure 7:
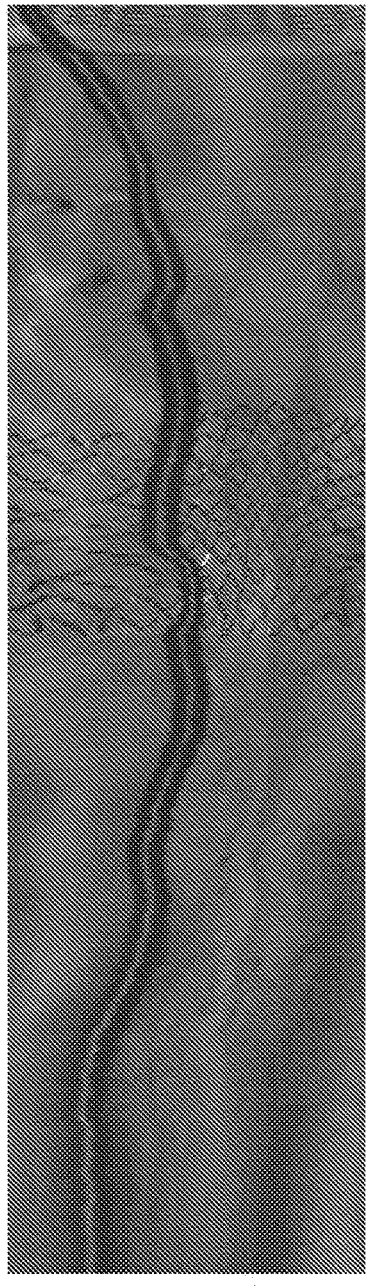
FIG. 7 illustrates an example carpet view image showing a two-dimensional representation of intravascular image data.

FIG. 7 illustrates an example carpet view image showing a two-dimensional representation of intravascular image data. The carpet view image having dimensions A×L, where A is the number of A-lines and L is the number of frames, is created by importing all images from a pullback and averaging each of the A-lines in every frame. Thus, each frame corresponds to a single vertical line in the carpet view image. Each vertical line in the carpet view image includes various intensity values corresponding to respective A-lines of each frame. FIG. 7 depicts contrasting intensity values between certain areas of the carpet view image. For example, the carpet view image includes contrasting intensity values in areas of metallic objects that cast shadows, such as stent strut shadows and guidewire shadows. Shadows of a guidewire object, for example, appear horizontally across the carpet view image of FIG. 7. Additionally, an area 701 in the carpet view image includes stent strut shadows in a visible pattern. The area 701 corresponds to a set of frames that include image data representative of the stent. For example, the frames in the area 701 correspond to respective vertical lines of the carpet view image at which stent strut shadows are shown.

In step S603, the computing system 101 generates a signal that represents the plurality of images included in the intravascular image data. For example, the computing system 101 may generate a signal that represents the plurality of images that correspond to the frames (L) of the 2D representation generated in step S602. In some embodiments, in step S603, the computing system 101 generates the signal by generating a respective signal value for each of a plurality of images in intravascular image data based on a respective group of A-lines corresponding to each of the plurality of images. In some embodiments, the computing system 101 generates the signal by averaging vertical lines of the carpet view image to obtain a respective average intensity value for each frame. An example of a signal generated in step S603 is shown in FIG. 8.

Figure 8:
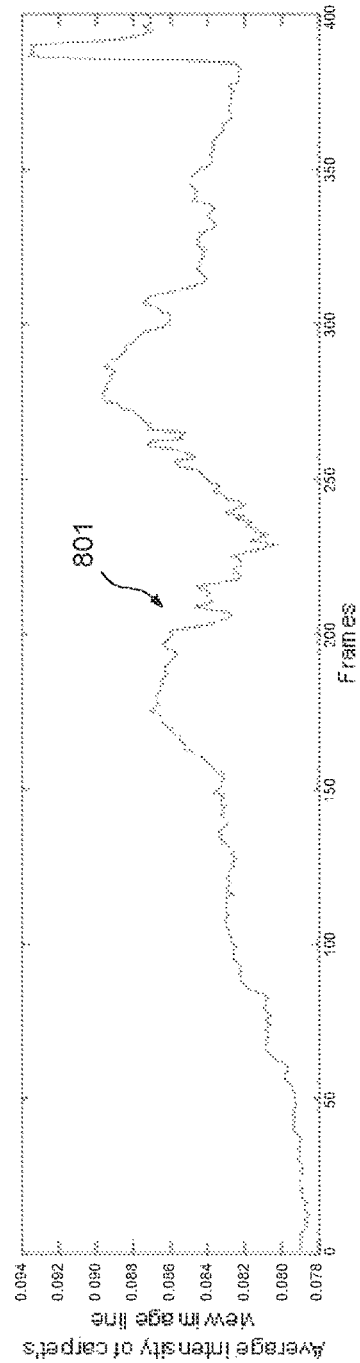
FIG. 8 illustrates an example signal generated based on the representation of intravascular image data of FIG. 7.

FIG. 8 illustrates a signal 801 created by averaging the vertical lines of the carpet view image of FIG. 7. In the example shown in FIG. 8, the signal 801 corresponds to 400 frames of image data, as indicated along the horizontal axis. Each frame includes an A-line image that corresponds to a respective vertical line of the carpet view image of FIG. 7. For example, each A-line image obtained in a pullback corresponds to a respective group of A-lines (e.g., based on a number of A-line scans per frame); and each group of A-lines corresponds to a respective vertical line of the carpet view image. As indicated with respect to step S602, the carpet view image is generated by averaging each of the A-lines in every frame. Thus, in the example shown in FIG. 7, the carpet view image includes 400 vertical lines arranged sequentially, corresponding to the 400 frames of A-line images. Each vertical line of the carpet view image includes various intensity values based on the respective A-lines associated with each A-line image. In FIG. 8, the signal 801 is a series of average intensity values, each intensity value corresponding to a respective vertical line of the carpet view image.

In some embodiments, in step S603, the computing system 101 determines representative information for each vertical line. The representative information may be any information that represents, corresponds to, identifies, or is associated with the vertical line, or the A-line image, or a feature or characteristic of the vertical line, or a feature or characteristic of the A-line image, or a combination of two or more of these. In some embodiments, the representative information is a single value. The computing system 101 may then use the respective representative information corresponding to each vertical line and/or A-line image to generate the signal 801. In some embodiments, each A-line image is represented by a respective signal value of the signal 801. In some embodiments, step S603 includes generating the signal 801 by averaging each vertical line of the carpet view image. For example, an average intensity value of each vertical line may be determined based on respective intensity values of A-lines associated with each vertical line. In some embodiments, the respective average intensity value corresponding to each vertical line of the carpet view image is used to generate the signal 801.

Accordingly, in some embodiments, each frame of image data corresponds to a respective signal value of the signal 801. For example, by averaging each vertical line of the carpet view image, a single value can be obtained for each frame of image data. The signal may then be created based on the respective signal values. By creating the signal in step S603 using the vertical lines of the carpet view image, according to some embodiments, each A-line image of the intravascular image data can be represented by a single value. This allows for processing of the whole pullback to locate the stent using only one signal in some embodiments, which can reduce the computational time relative to conventional methods. For example, in some embodiments, using the signal generated in step S603 to locate a stent within a vessel reduces computational time compared to performing stent detection by scanning the whole arterial pullback, for example, to detect all individual stent struts seen in the 2D images.

In FIG. 8, the signal 801 representing the average intensity of carpet view image vertical lines steadily increases for about the first 150 frames. As the frame number approaches the edge or boundary of the stent, there is a sharp rise in the average intensity as indicated by the signal 801 between frame 150 and frame 200. The area 701 of FIG. 7 that includes stent strut shadow patterns corresponds to an increase in fluctuations of the signal 801. That is, there is a spike in average intensity of carpet view image vertical lines positioned at the edges or boundaries of the stent (e.g., positions at which the stent starts and the stent ends), and there are sharper and more frequent fluctuations in average intensity within the area 701 that includes stent strut shadows. The area 701 that includes patterns of stent strut shadows extends to between frame 250 and frame 300. Outside of the area 701 corresponding to the stent, the average intensity steadily decreases as indicated by the signal 801 from about frame 300 to frame 380 in FIG. 8.

In step S604, the computing system 101 divides the signal 801 into signal segments. In some embodiments, the computing system 101 divides the signal 801 into signal segments based on a predetermined number of signal values for each signal segment. For example, the signal 801 may be divided into one or more signal segments each having 10 signal values. In one or more embodiments, the computing system 101 divides the signal 801 into signal segments that include at least one signal segment that corresponds to at least ten images. For example, in some embodiments, each A-line image of the 400 frames is represented by a respective signal value in the signal 801 generated in step S603, and the computing system 101 divides, in step S604, the signal 801 into signal segments having ten signal values each. Accordingly, each signal segment may include ten signal values that correspond to ten A-line images, each of the ten signal values representing a respective one of the ten A-line images.

In some embodiments, each of the signal segments corresponds to two or more sequential images of the plurality of images in the intravascular image data. For example, each of the signal segments may correspond to two or more A-line images of sequential frames. In some embodiments, signal segments may be any suitable size, and any suitable basis or criteria may be used for dividing the signal 801. In some embodiments, the signal 801 is divided such that each signal segment of the signal 801 is equal in size to each other signal segment of the signal 801. In some embodiments, the signal 801 is divided such that at least a first signal segment of the signal 801 is a different size than at least a second signal segment of the signal 801. Examples of signal segments generated in step S604, according to some embodiments, are shown in FIG. 9.

Figure 9:
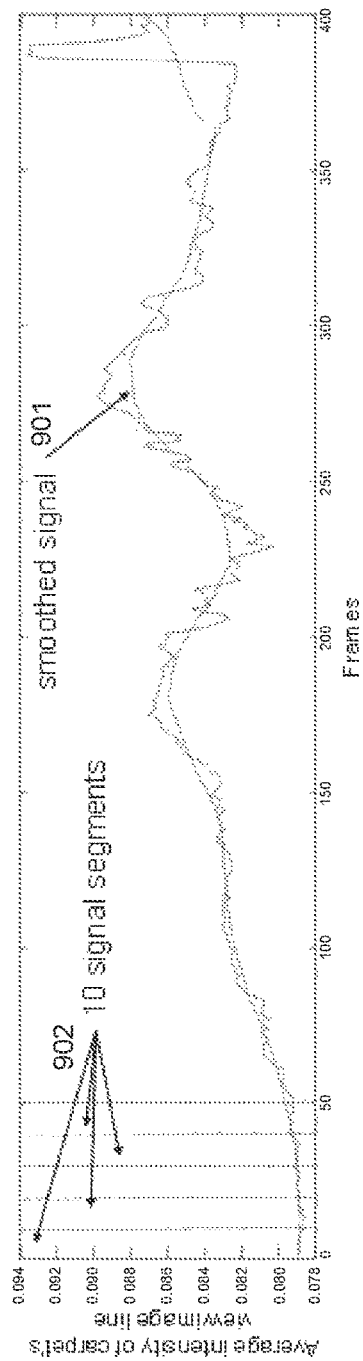
FIG. 9 illustrates an example of a moving average smoothed signal superimposed on the signal of FIG. 8 and illustrates example signal segments.

FIG. 9 illustrates five example signal segments 902. Additionally, FIG. 9 illustrates a moving average smoothed signal 901 that is superimposed on the signal 801 of FIG. 8. By way of example, FIG. 9 depicts the signal 801 and the moving average smoothed signal 901 divided into five signal segments 902. Each of the signal segments 902 corresponds to 10 respective frames (frames 1-10, 11-20, 21-30, 31-40, and 41-50) in FIG. 9. Although the example of FIG. 9 shows five signal segments 902 over a particular section (frames 0 to 50) of the signal data for clarity of description, the disclosure is not limited to the example(s) in FIG. 9. The disclosure contemplates any suitable number of signal segments 902 over all or a portion of signal data. In some embodiments, the entirety of the signal 801 and the moving average smoothed signal 901 in FIG. 9 are divided in signal segments 902. For example, in some embodiments, the signal 801 and the moving average smoothed signal 901 are divided in 40 equal signal segments 902 over the 400 frames of FIG. 9, each signal segment corresponding to a respective set of 10 frames.

In step S605, the computing system 101 extracts one or more signal features of each signal segment. According to one or more embodiments, the computing system 101 extracts a low-state level and a high-state level for each signal segment. For example, in some embodiments, the computing system 101 extracts, for each signal segment, the low-state level and the high-state level in the bi-level waveform of the signal segment using the histogram method. According to one or more embodiments, the computing system 101 extracts, for each signal segment, a signal-to-noise ratio between the signal segment and its moving average smoothed signal. For example, as indicated in FIG. 9, a moving average smoothed signal 901 may be generated by calculating a moving average using respective signal values of the signal 801. Any suitable method or variation of moving average may be used to generate the moving average smoothed signal 901. Then, for each signal segment, the signal-to-noise ratio between the signal segment and the corresponding moving average smoothed signal is extracted.

According to one or more embodiments, in step S605, at least the following three signal features are extracted: the low-state and high-state levels in the bi-level waveform of the signal segment using the histogram method and the signal-to-noise ratio between the signal segment and its moving average smoothed signal. For example, in some embodiments, a set of features is extracted for each signal segment, where the set of features includes at least the three signal features above. In some embodiments, one or more features extracted in step S605 may be used by a machine learning model. For example, one or more of the extracted features may be used to train a machine learning model. Further by way of example, one or more of the extracted features may be used by the machine learning model to classify one or more inputs provided to the machine learning model.

In step S606, the computing system 101 inputs signal segment feature data into a classifier. In one or more embodiments, step S606 includes inputting, into the classifier, one or more signal features extracted in step S605. In one or more embodiments, the classifier is a machine learning model. For example, the classifier may be a Support Vector Machine (SVM) classifier. In some embodiments, the classifier is configured to output a classification for a signal segment as either representative of image data of an endovascular device (e.g., a stent) or, alternatively, not representative of image data of the endovascular device. In one or more embodiments, the classifier is a trained classifier and the classification for the signal segment is based on one or more signal features included in the signal segment feature data. An example operational flow for training a machine-learning model, and example training data for the training of the machine-learning model are described further below with reference to FIGS. 29 and 30.

According to one or more embodiments, in step S606, the computing system 101 inputs into the classifier a low-state level and a high-state level of a signal segment, and a signal-to-noise ratio between the signal segment and a moving average smoothed signal for the signal segment. In some embodiments, the signal segment is classified by the classifier based on the low-state and high-state levels in the bi-level waveform of the signal segment using the histogram method and the signal-to-noise ratio between the signal segment and its moving average smoothed signal. For example, a Support Vector Machine (SVM) may be used to classify each signal segment (using their respective feature values) to stent or not. In some embodiments, each of the signal segments 902 described with reference to step S604, in which the signal 801 is divided into the signal segments 902, is classified by the classifier. For example, signal segments 902 of respective 10-value signals may be classified to stent or not based on the signal segment feature data input into the classifier at step S606.

In step S607, the classifier outputs a classification for each signal segment as either representative of image data of the endovascular device or, alternatively, not representative of image data of the endovascular device. For example, in some embodiments, a Support Vector Machine (SVM) is used to classify the signal segments 902 (using feature values corresponding to each signal segment extracted in step 605) to stent or not. According to one or more embodiments, each signal segment is classified as a stent segment or not a stent segment. By way of example, one or more signal segments classified as representative of image data of the endovascular device are signal segments that correspond to one or more frames in the area 701 of the carpet view image at which stent strut shadows patterns are visible.

According to one or more embodiments, in step S607, the trained classifier outputs the classification for each of the signal segments 902 based on one or more signal features including, for example, the low-state and high-state levels in the bi-level waveform of the signal segment using the histogram method and the signal-to-noise ratio between the signal segment and its moving average smoothed signal. As illustrated in FIGS. 7 and 8, the area 701 that includes stent strut shadow patterns corresponds to an increase in fluctuations of the signal 801. That is, there is a spike in average intensity of carpet view image vertical lines positioned at the edges or boundaries of the stent (e.g., positions at which the stent starts and the stent ends), and there are sharper and more frequent fluctuations in average intensity within the area 701 that includes stent strut shadows. Moreover, as depicted in FIG. 9, when the moving average smoothed signal 901 is superimposed on the signal 801, the region of the signal 801 corresponding to the area 701 of the carpet view image includes a higher signal-to-noise ratio than other regions of the signal 801. For example, for many of the signal segments corresponding to frames in the area 701 of the carpet view image, a difference between the signal segment and its moving average smoothed signal 901 is larger than for many of the signal segments that correspond to frames outside of the area 701 of the carpet view image. Based on the fluctuations of the signal 801 for frames corresponding to the area 701 of the carpet view image, various features of the signal segments that correspond to the area 701 of the carpet view image may include distinct characteristics compared to the corresponding features of signal segments that correspond to frames outside the area 701 of the carpet view image. For example, features such as the low-state level and the high-state level of signal values in a signal segment and signal-to-noise ratio for a signal segment can be used to identify signal segments as either representative of image data of the endovascular device or, alternatively, not representative of image data of the endovascular device. That is, based on the training of the classifier described in FIGS. 29 and 30, signal segments which represent frames corresponding to the area 701 of the carpet view image may be distinguished from signal segments which represent frames corresponding to regions of the carpet view image outside the area 701 based on an analysis of the low-state and high-state levels in a signal segment and the signal-to-noise ratio of the signal segment.

If the classifier outputs a classification of a signal segment as representative of image data of an endovascular device (Yes in step S607), the flow proceeds to step S608. For example, in some embodiments, a signal segment is classified to stent segment based on the signal segment feature data of the signal segment. On the other hand, if the classifier outputs a classification of a signal segment as not representative of image data of the endovascular device (No in step S607), the flow proceeds to step S609. For example, in some embodiments, a signal segment is classified to not stent segment based on the signal segment feature data of the signal segment.

In step S608, the computing system 101 identifies image(s) that correspond to the stent. In some embodiments, the frames of the pullback sequence that correspond to the stent segment are identified as containing images that correspond to the stent. That is, the signal segments classified as representative of image data of an endovascular device in step S607 are identified as stent frames. In one or more embodiments, based on the classification of one or more signal segments as representative of image data of the endovascular device, the computing system 101 identifies one or more images corresponding to the one or more signal segments as the one or more images that correspond to the endovascular device. Accordingly, the computing system 101 identifies, in the plurality of images of a pullback sequence, one or more images that correspond to the endovascular device based on the signal 801 that represents the plurality of images.

In some embodiments, signal segments which represent frames corresponding to the area 701 of the carpet view image are identified as containing stent frames which indicate the stent position within the vessel. By way of example, the signal segments 902 which correspond to the frames corresponding to the area 701 of the carpet view image may include about 50 to 80 frames (from about frame 190 to about frame 270). These frames corresponding to the area 701 of the carpet view image are more likely to be classified as representative of image data of the endovascular device (i.e., classified as a stent segment) than frames outside the area 701 of the carpet view image based on the fluctuations of intensity measurements for this region of frames. After the computing system 101 identifies image(s) that correspond to the stent in step S608, the flow proceeds to step S609.

In step S609, the computing system 101 determines whether another segment is present that needs to be classified, among the segments generated by dividing the signal 801 into signal segments 902. If another signal segment 902 is present that has not yet been classified (Yes in step S609), the flow proceeds to step S606. For example, the identified signal segment 902 that has yet to be classified is analyzed. That is, the signal segment feature data is input into the classifier for the identified signal segment in step S606 and the classification at step S607 is repeated for the signal segment 902. On the other hand, if the computing system 101 determines that no other signal segment 902 needs to be classified (No in step S609), the flow proceeds to S1001 of FIG. 10.

Accordingly, for each of the signal segments 902 of the signal 801 divided in step S604, feature data extracted in step S605 is input into the classifier in step S606 and each signal segment is classified in step S607 as a stent segment or not a stent segment. By creating the signal 801 and applying a machine learning model (e.g., SVM classifier), a stent area is located and stent detection can be applied only in this area (e.g., area corresponding to area 701 of the carpet view image), thus reducing the processing time. By virtue of the above processes, the present disclosure uses machine learning on the signal 801 to locate the stent area 701 in the carpet view image. The use of machine learning on the signal 801 to locate the stent reduces the feature extraction dimensionality and the computational time compared to searching all frames of the pullback sequence. In one or more embodiments, thus, include detecting automatically the endovascular device (stent) position within the intravascular pullback. The frames of the pullback that correspond to the stent segment of the carpet view image may then be further analyzed, as described with reference to FIG. 10.

Figure 10:
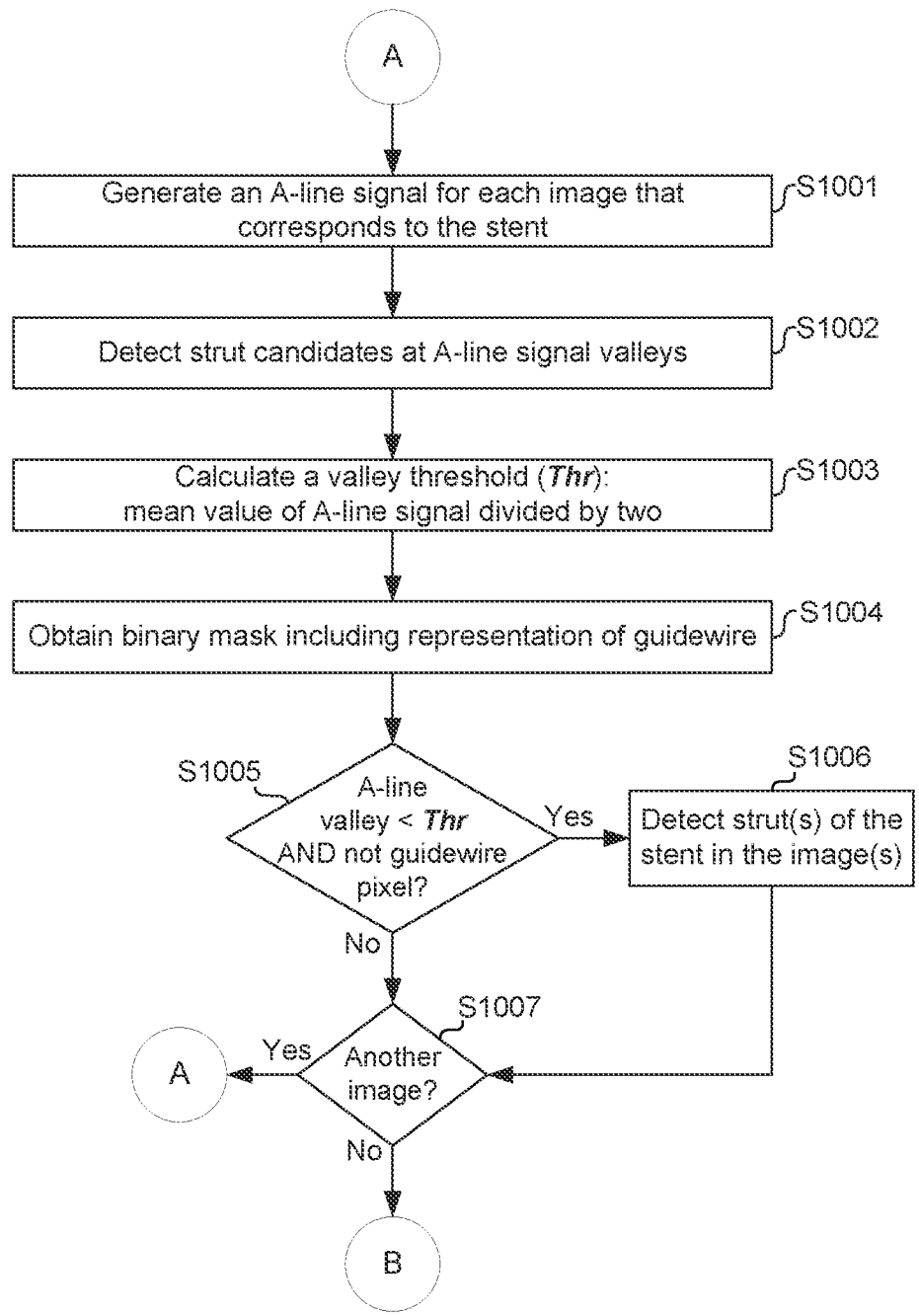
FIG. 10 illustrates an example operational flow for use in stent detection.

FIG. 10 illustrates an example operational flow for use in stent detection. In some embodiments, one or more of the steps of FIG. 10 are performed at the computing system 101 by executing program instructions of the application(s) 112 on the computing system 101.

In step S1001, the computing system 101 generates an A-line signal for the image(s) that correspond to the stent. For example, each of the images identified in step S608 as corresponding to the stent are further analyzed by generating a respective A-line signal for each image. For each of the one or more images that correspond to the endovascular device, the computing system 101 generates an A-line signal by averaging A-lines of the A-line image. An example A-line image is shown in FIG. 11.

Figure 11:
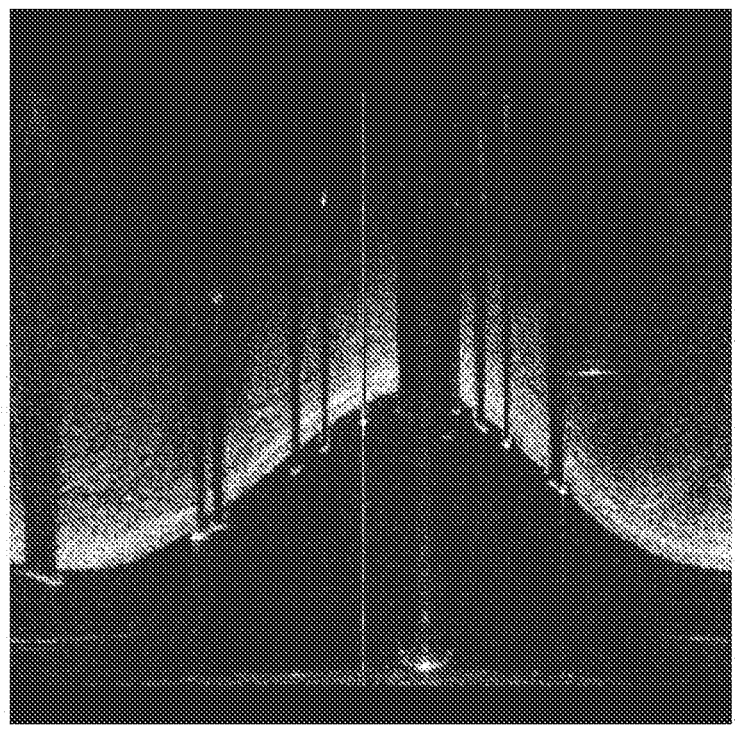
FIG. 11 illustrates an example of an A-line image.

FIG. 11 illustrates an example of an A-line image representing stent struts. For example, a polar OCT image is depicted showing detected stent struts. The detected stent struts appear as bright formations followed by a shadow since light does not penetrate the metallic structure of a stent strut. In some embodiments, in step S1001, for each frame corresponding to the area 701 of the carpet view image, an A-line signal is created by averaging each frame's A-line. The computing system 101 then analyzes the A-line signal of the stent frames.

Figure 12:
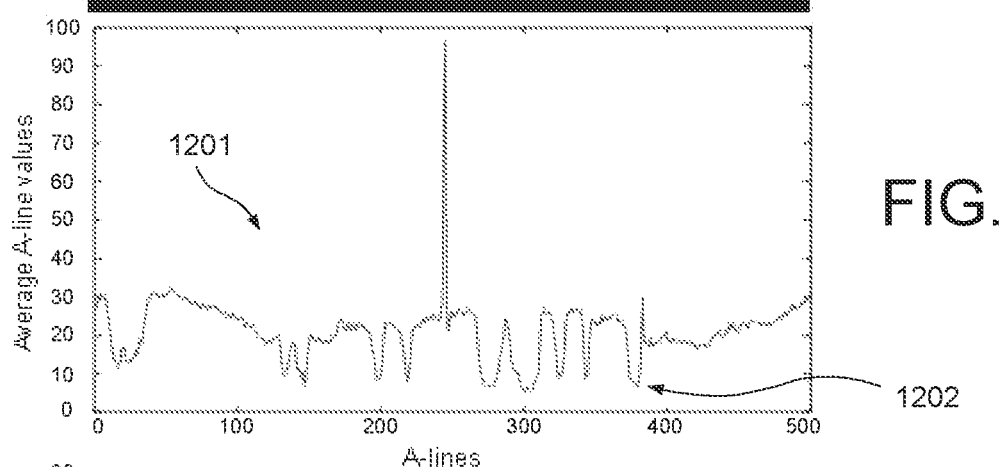
FIG. 12 illustrates an example A-line signal that corresponds to the A-line image depicted in FIG. 11.

FIG. 12 illustrates an A-line signal 1201 corresponding to the A-line image of FIG. 11. The A-line signal 1201 indicates average A-line values and includes a plurality of peaks and valleys. An example valley 1202 shown in FIG. 12 represents a stent strut corresponding to one of the detected stent struts that is shown in FIG. 11.

In step S1002, the computing system 101 detects strut candidates at A-line signal valleys. In some embodiments, the computing system 101 detects strut candidates of an endovascular device at respective A-line signal valleys, as shown in FIG. 13.

Figure 13:
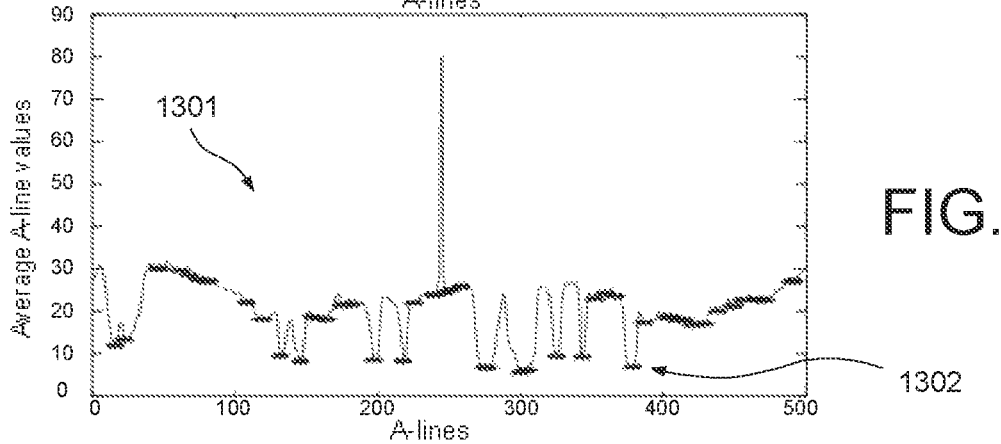
FIG. 13 illustrates detected valleys of the A-line signal of FIG. 12, each detected valley corresponding to a candidate stent strut.

FIG. 13 illustrates detected valleys of an A-line signal 1301 corresponding to the A-line signal 1201 of FIG. 12, with each detected valley of the A-line signal 1301 corresponding to a stent candidate A-line. The detected valleys of the A-line signal 1301 are each indicated with an asterisk (*). For example, the example detected valley 1302 marked with an asterisk in FIG. 13 corresponds to the valley 1202 depicted in FIG. 12. The example detected valley 1302 is one of several detected valleys along the A-line signal 1301 of FIG. 13.

In step S1003, the computing system 101 calculates a valley threshold (Thr) for the A-line signal. In some embodiments, the valley threshold (Thr) is the mean value of the A-line signal 1201 divided by two. The computing system 101 calculates the valley threshold (Thr) by determining the mean value of the average A-line values that make up the A-line signal 1201, and dividing the mean value by two. In some embodiments, the computing system 101 automatically calculates the valley threshold (Thr). According to one or more embodiments, the valley threshold (Thr) may then be used to detect stent struts. By way of example, in the A-line signal 1301 of FIG. 13, a portion of the detected valleys (marked with an asterisk) positioned below a calculated valley threshold (Thr) are considered stent strut candidates.

In step S1004, the computing system 101 obtains a binary mask including a representation of a guidewire. By way of example, detecting the guidewire and its shadows is used to improve stent strut detection. Detecting a known shadow, the guide guidewire, reduces false positives. Thus, by detecting the guidewire shadow in advance of stent strut processing, the guidewire shadow can be excluded from strut detection.

In one or more embodiments, the computing system 101 creates a binary carpet view image using an auto-thresholding method (e.g., Otsu automatic threshold method, k-means method). The carpet view image is filtered using bilateral filtering and automatically binary segmented using, for example, Otsu's automatic threshold method. Using the segmented image, the object penetrating the carpet view image is defined as the guidewire object.

Figure 14:
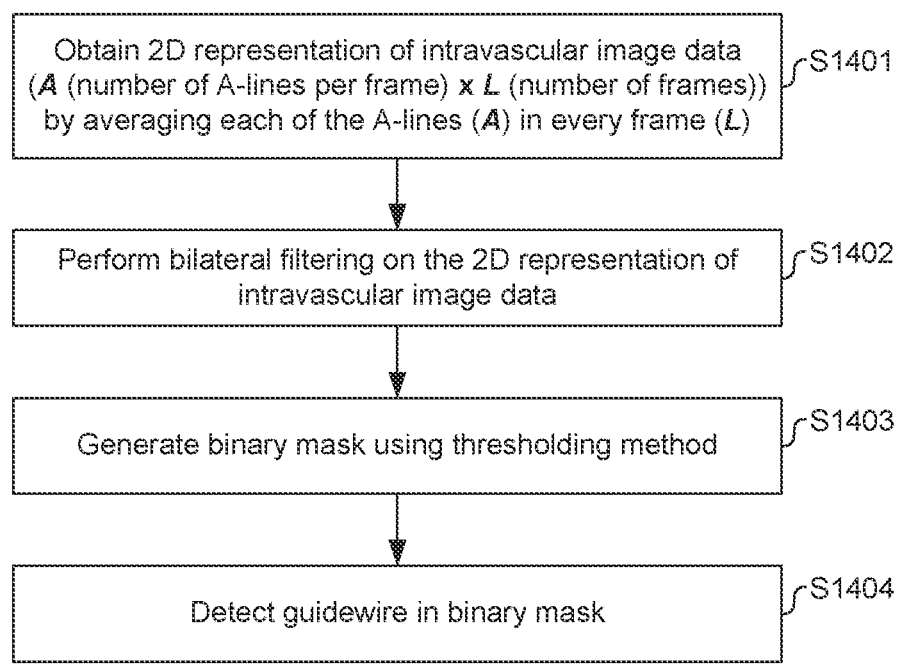
FIG. 14 illustrates an example operational flow for use in stent detection.

In one or more embodiments, step S1004 is carried out by performing the steps shown in FIG. 14. FIG. 14 illustrates an example operational flow for use in stent detection. In some embodiments, one or more of the steps of FIG. 14 are performed at the computing system 101 by executing program instructions of the application(s) 112 on the computing system 101. The steps of FIG. 14 are described with reference to FIGS. 15A-15C.

Figures 15A, 15B, 15C:
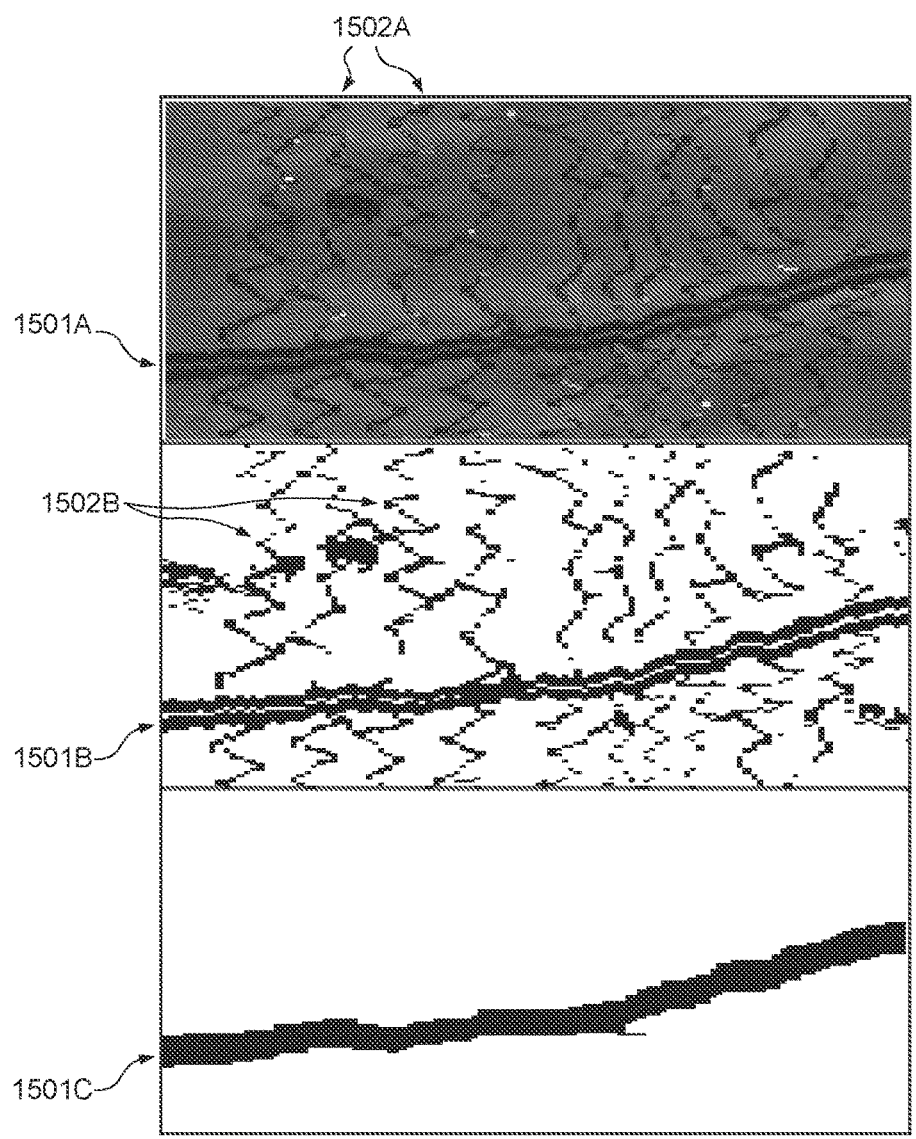
FIGS. 15A-15C illustrate example carpet view images at different stages of processing.

FIGS. 15A-15C illustrate a carpet view image at different stages of filter processing. FIG. 15A illustrates a carpet view image. FIG. 15B illustrates the corresponding binary image after applying automatic thresholding. FIG. 15C illustrates a detected guidewire object.

In step S1401, the computing system 101 obtains a 2D representation of intravascular image data having dimensions A×L, where A is the number of A-lines per frame and L is the number of frames. In one or more embodiments, step S1401 comprises obtaining the carpet view image generated in step S602. According to one or more embodiments, step S1401 includes obtaining a portion of the carpet view image generated in step S602.

In one or more embodiments, step S1401 includes using a 2D representation of the intravascular image data to generate a binary mask that includes a representation of a guidewire. FIG. 15A shows the carpet view image including a representation of a guidewire 1501A. Additionally, FIG. 15A includes stent strut shadows in a visible pattern showing a representation of a stent 1502A.

In step S1402, the computing system 101 performs bilateral filtering on the 2D representation of intravascular image data. For example, similarly to Gaussian filters, bilateral filters are non-linear smoothing filters. Their fundamental difference is that they take into account the pixels intensity differences which result to edge maintenance simultaneously with noise reduction. Using convolutions, a weighted average of the neighborhood pixels intensities replace the intensity of the mask's central pixel. The bilateral filter for an image I, and a window mask W is defined as:

$$I'(x) = \frac{1}{W_p} \sum_{x_i \in W} I(x_i) f_r(\|I(x_i) - I(x)\|) g_s(\|x_i - x\|),$$

having a normalization factor $$W_p \colon W_p = \Sigma_{x_i \in W} f_r(\|I(x_i) - I(x)\|) g_s(\|x_i - x\|),$$

where x are the coordinates of the mask's central pixel and the parameters $f_r$ and $g_s$ are the Gaussian kernel for smoothing differences in intensities and the spatial Gaussian kernel for smoothing differences in coordinates.

FIG. 15B shows the carpet view image after having image bilateral filtering performed thereon. In FIG. 15B, a representation of a guidewire 1501B is shown. Moreover, FIG. 15B includes stent strut shadows in a pattern showing a representation of a stent 1502B.

In step S1403, the computing system 101 generates a binary mask using a thresholding method. For example, in some embodiments, using a 2D representation of the intravascular image data, the computing system 101 generates a binary mask that includes a representation of a guidewire.

To automatically threshold the carpet view image, a threshold $Thr_{otsu}$ for the image I' is calculated using the Otsu's method, and the pixels of the image I' that are smaller than $Thr_{otsu}$ are set to zero value. The result is a binary image with the guide wire represented by the zero objects. For example, FIG. 15C illustrates the detected guidewire object 1501C as an image after having been automatically binary segmented using Otsu's automatic threshold method. In some embodiments, another method is utilized for performing the automatic thresholding. For example, k-means method may be used in some embodiments to perform automatic thresholding.

In step S1404, the computing system 101 detects the guidewire object 1501C in the binary mask shown in FIG. 15C. In some embodiments, step S1404 includes detecting the guidewire in an image that corresponds to the endovascular device based on the binary mask, and excluding or removing the guidewire from the image. By detecting the catheter guidewire object 1501C in the binary carpet view image, the guidewire artifact can be separated from the stent struts increasing the strut detection accuracy. Guidewire removal using the carpet view image can thus be performed using the steps of FIG. 14. Moreover, processing the carpet view image to detect the guidewire artifact can be performed quickly and accurately for both stented and un-stented pullback sequences. Thus, according to one or more embodiments, the step S1004 is carried out using the process described with reference to FIGS. 14 and 15.

Figures 16, 17:
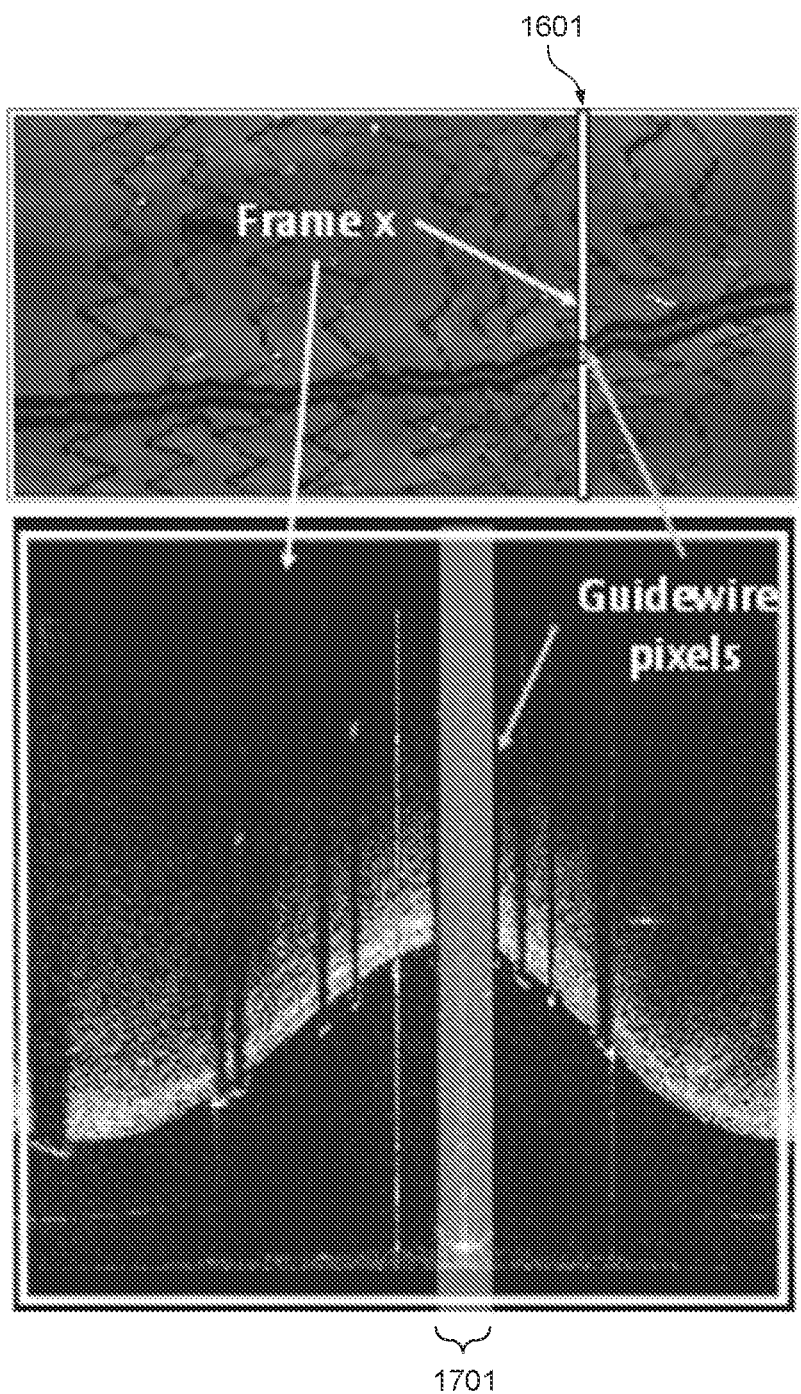
FIG. 16 illustrates an example carpet view image.
FIG. 17 illustrates an example A-line image of Frame X (depicted in FIG. 16 as a vertical white line).

Still referring to step S1004, a correspondence between a frame and its guidewire pixels and the carpet view image is shown in FIGS. 16 and 17. FIG. 16 illustrates a carpet view image, having a white vertical line 1601 corresponding to the image Frame X (shown in FIG. 17). The small gray segment (bisecting the vertical white line 1601) shown in FIG. 16 corresponds to the guidewire pixels. FIG. 17 illustrates the correspondence between a frame (A-line image labeled Frame X) and its guidewire pixels 1701 (gray strip in the A-line image).

As shown with reference to FIGS. 16 and 17, each A-line image corresponds to a frame (e.g., Frame X). Each frame corresponds to a single line of the carpet view image (as shown by the vertical white line 1601 in FIG. 16). And the portion of each frame that overlaps the guidewire (as indicated by the gray strip) 1701 indicates the guidewire pixels which may be excluded or removed from stent strut candidates detected in step S1002.

In step S1005, the computing system 101 determines, for each strut candidate detected at an A-line signal valley in S1002, whether the A-line valley is less than the valley threshold (Thr) calculated in step S1003 and, in addition, does not belong to a guidewire pixel identified in step S1004. According to one or more embodiments, the computing system 101 detects one or more struts based on the determination that each of the one or more struts corresponds to a respective A-line signal valley that is less than the valley threshold and does not belong to a guidewire pixel. For example, if an A-line valley, such as detected valley 1302, is less than the calculated valley threshold (Thr) and does not belong to pixel of guidewire object, such as guidewire pixels 1701, then the A-line valley belongs to a stent A-line.

Figure 18:
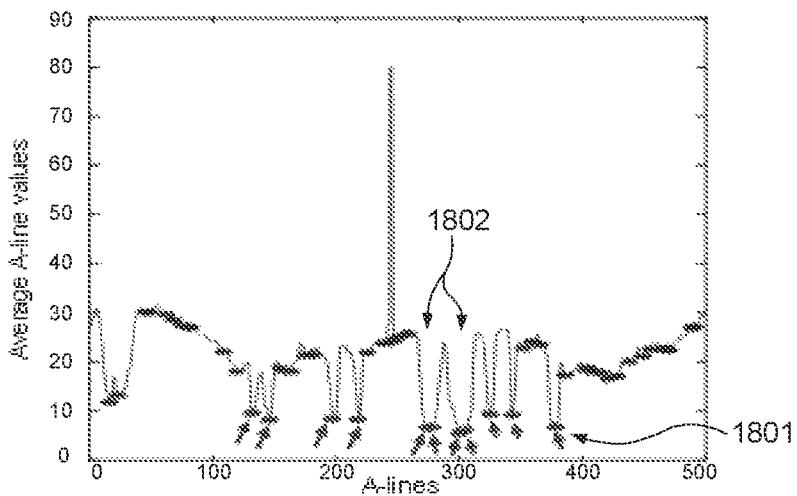
FIG. 18 illustrates an example A-line signal and detected stent struts.
Figure 19:
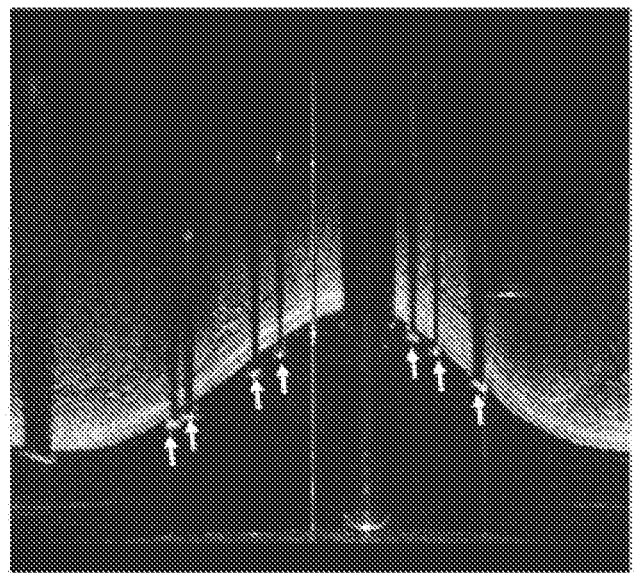
FIG. 19 illustrates a polar OCT image showing the detected stent struts of FIG. 18.
Figure 20:
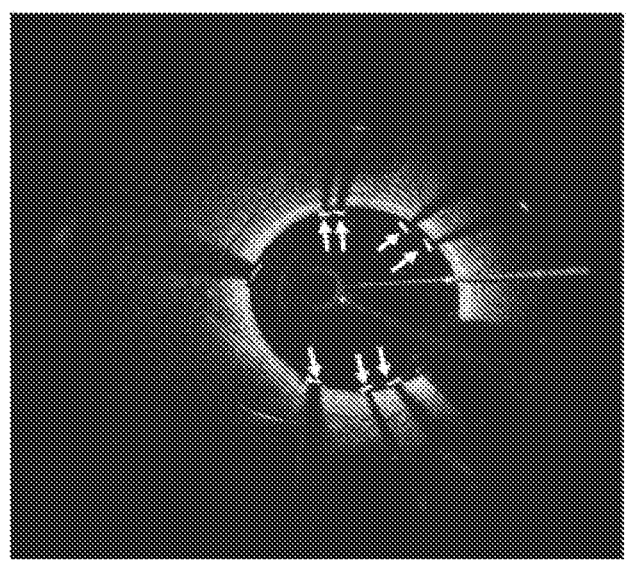
FIG. 20 illustrates a Cartesian OCT image showing the detected stent struts of FIG. 18.

FIGS. 18-20 illustrate a stent strut detection example. FIG. 18 illustrates an A-line signal of an A-line image corresponding to the A-line image shown in FIGS. 19 and 20. In the A-line signal of FIG. 18, each of the valleys is marked with an asterisk (*). Eleven of the valleys (*) are found to be below the valley threshold (Thr) calculated in step S1003. These eleven valleys are identified by the eleven arrow symbols in FIG. 18. That is, of all the valleys (*) detected in step S1002, only eleven valleys were found to be below the valley threshold (Thr) calculated in step S1003. An example valley 1801 below the valley threshold (Thr) is shown as being identified by an arrow. Of the eleven valleys identified by arrows in FIG. 18, four of the valleys 1802 belong to a guidewire object pixel. For example, the four valleys 1802 identified in FIG. 18 belong to guidewire pixels 1701 such as shown in FIG. 17. Thus, in step S1005, only seven valleys (identified by arrows) are found to be A-line valleys which are both less than the calculated valley threshold (Thr) and do not belong to a guidewire pixel. These seven valleys are shown in FIGS. 19 and 20.

FIG. 19 illustrates an example A-line image corresponding to FIG. 18 and showing the A-lines belonging to stent struts. The maximum intensity pixel of the stent A-lines is the stent strut. In FIG. 19, a polar OCT image is shown, with arrows identifying the seven detected stent struts. FIG. 20 shows a Cartesian OCT image with the detected struts corresponding to FIG. 19.

In step S1005, for each A-line image, if any A-line valley(s) is/are found to be less than the threshold valley (Thr) and not belonging to a guidewire pixel (Yes in step S1005), the flow proceeds to step S1006. On the other hand, if for an A-line image no A-line valley is found which is less than the threshold valley (Thr) and does not below to a guidewire pixel (No in step S1005), the flow proceeds to step S1007.

In step S1006, the computing system 101 detects strut(s) of the stent in the A-line image(s). In some embodiments, the computing system 101 detects, for each of the one or more images that correspond to the endovascular device, respective one or more struts of the endovascular device. The stent struts are detected as the brightest pixels of the A-lines that correspond to valleys which are less than the valley threshold (Thr) and do not belong to a guidewire object pixel. According to one or more embodiments, to detect the stent struts, the computing system 101 finds the max intensity of the stent line and designates it as a stent strut. For example, in the example shown in FIG. 19, seven stent struts are detected by detecting the brightest pixel of the seven A-lines identified as valleys which are less than the valley threshold (Thr) and do not belong to a guidewire object pixel. The seven detected stent struts are identified by white arrows in FIG. 19, for example. After the computing system 101 detects strut(s) of the stent in the A-line image(s), the flow proceeds to step S1007.

In step S1007, the computing system 101 determines whether another A-line image is present that has not been analyzed to detect stent strut(s). For example, in some embodiments, the computing system 101 determines whether, among the images identified in step S608 as corresponding to the stent, there is any remaining image(s) that has not yet been analyzed to detect stent strut(s). If another A-line image is present that has not yet been analyzed for stent strut(s) (Yes in step S1007), the flow proceeds to step S1001. For example, the identified A-line image that has not yet been analyzed is analyzed by repeating the steps of FIG. 10. On the other hand, if the computing system 101 determines that no other A-line image needs to be analyzed (No in step S1007), the flow proceeds to S2101 of FIG. 21.

Figure 21:
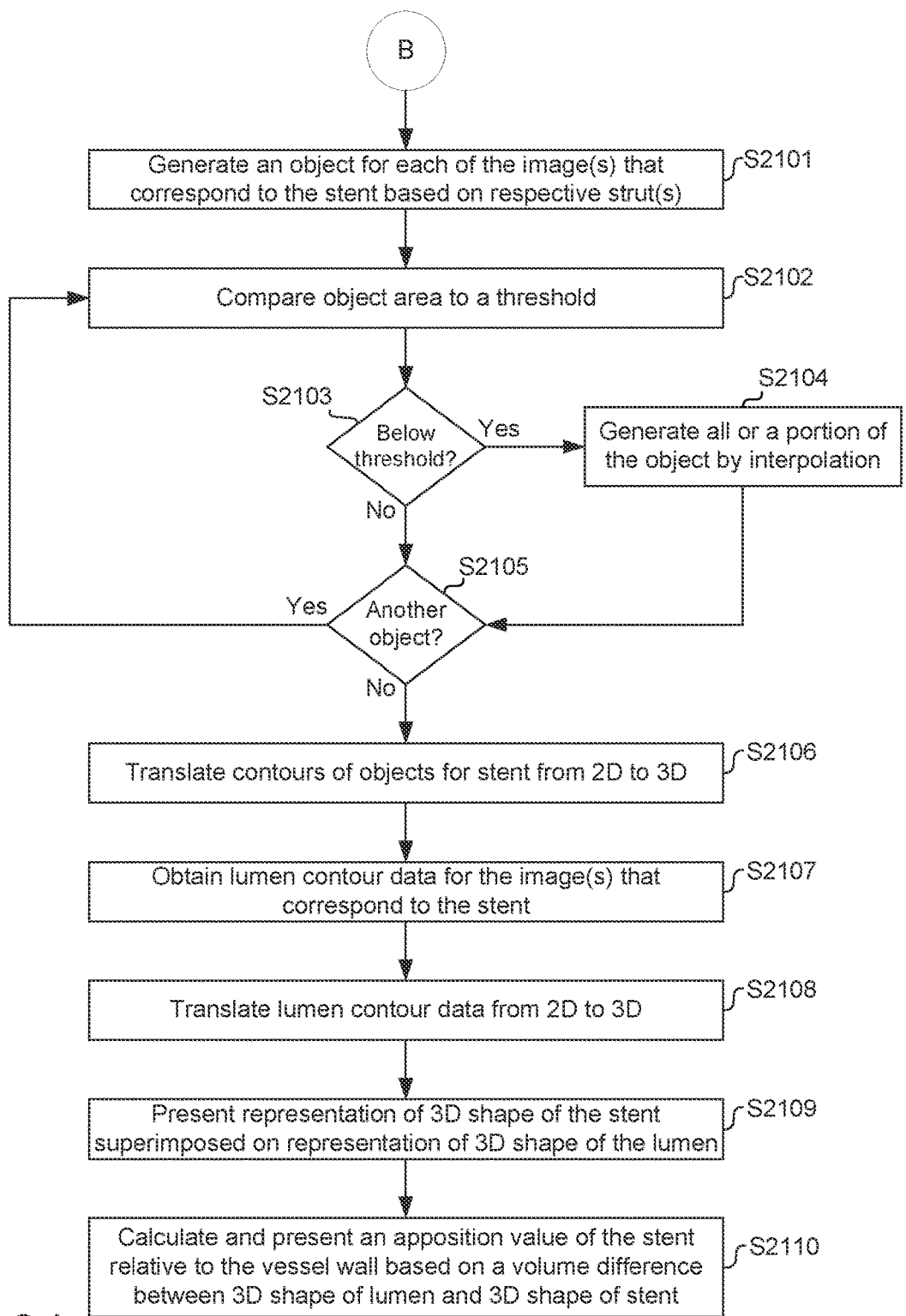
FIG. 21 illustrates an example operational flow for use in stent apposition measurement.

FIG. 21 illustrates an example operational flow for use in stent apposition measurement. In some embodiments, one or more of the steps of FIG. 21 are performed at the computing system 101 by executing program instructions of the application(s) 112 on the computing system 101.

In step S2101, the computing system 101 generates an object for each of the image(s) that correspond to the stent based on respective strut(s). In one or more embodiments, the computing system 101 generates a respective object for each of the one or more images that correspond to the endovascular device, each object representing a respective surface segment of the endovascular device. For example, in some embodiments, an object is generated for each of the image(s) identified in step S608 where the contours of each object are based on respective struts detected in step S1006 for each image.

In one or more embodiments, step S2101 includes generating a plurality of objects by applying a respective spline over the respective one or more struts for each of the plurality of the objects, wherein the plurality of the objects represent successive surface segments of the endovascular device. For example, using the detected struts for each image, a spline is applied creating binary objects representing the surface of the stent in each image.

In step S2102, the computing system 101 compares an object area to a threshold. For example, in some embodiments, an area of each object is checked to determine if the object satisfies one or more criteria. In some embodiments, the computing system 101 compares a size of each object to a threshold value. For example, in one or more embodiments, if a binary object has an area less than 90% of its previous object, the computing system 101 determines that the object is below a threshold.

Any suitable threshold or criteria may be used in the comparison in step S2102. By way of example and not by way of limitation, an area of an object may be compared to an area of a successive object that is arranged immediately prior to or immediately subsequent to the object being checked, or an area of an object may be compared to a predetermined area size as a threshold, or the shape of the object may be compared to a predetermined shape. Alternatively, the threshold in step S2102 may be a threshold number of detected stent struts. For example, in step S2102, the computing system 101 may compare the number of stent struts that were detected and used to generate the object to a predetermined amount of stent struts as the threshold.

In step S2103, the computing system 101 determines whether the relevant object feature is below the threshold. For example, in some embodiments, the computing system 101 determines if the area of the object is below a threshold. In one or more embodiments, if a binary object has an area less than 90% of the previous object, the computing system 101 determines that the object is below a threshold. Alternatively, the computing system 101 may determine whether a shape of the object is not within a threshold amount of a predetermined shape. Alternatively, the computing system 101 may determine whether a number of stent struts used to generate the object is less than a predetermined amount. Any suitable threshold feature and any suitable threshold value may be implemented in step S2103.

If the object feature is below the threshold (Yes in step S2103), the flow proceeds to step S2104. On the other hand, if the object feature is not below the threshold (No in step S2103), the flow proceeds to step S2105.

In step S2104, the computing system 101 generates the object, determined to be below the threshold in step S2103, by interpolating one or more missing struts of the object using one or more struts of a second object and one or more struts of a third object. For example, when a size of a first object is below the threshold, the computing system 101 may interpolate one or more missing struts of the first object using one or more struts of a second object and one or more struts of a third object. By way of example, in some embodiments, if a binary object has an area less than 90% of its previous object, then the computing system 101 may re-calculate this object by interpolating the points of the pre and post frame's objects.

In some embodiments, step S2104 includes generating all or a portion of the object by interpolation. For example, in one or more embodiments, the computing system 101 generates a first object by interpolating one or more portions of the first object using data of a second object representing a preceding surface segment of the endovascular device relative to the first object, or using data of a third object representing a succeeding surface segment of the endovascular device relative to the first object, or using both the data of the second object and the data of the third object. In some embodiments, the computing system 101 generates the first object by interpolating one or more missing struts of the first object using one or more struts of the second object and one or more struts of the third object when the size of the first object is below the threshold. By way of example, the missing or not detected struts of a frame may be interpolated using the pre and post frame struts. The computing system 101 may recalculate this object by interpolating the points of the pre and post frame's objects. In one or more embodiments, the computing system 101 may average missing struts of a frame using the pre and post frame struts and connect them using a spline.

By way of example, and not by way of limitation, a stent struts interpolation example is shown schematically in FIGS. 22A-22C and FIGS. 23A-23C. FIGS. 22A-22C illustrate three sequential binary frames each showing stent struts (stars) and a corresponding object (white) created using a spline over the stent struts. For example, FIG. 22A illustrates a frame including six stent struts (stars) having been detected and a corresponding object (white) created using a spline over the six stent struts. FIG. 22B illustrates a frame including three stent struts (stars) having been detected and a corresponding object (white) created using a spline over the three stent struts. FIG. 22C illustrates a frame including five stent struts (stars) having been detected and a corresponding object (white) created using a spline over the five stent struts.

FIGS. 23A-23C illustrate three sequential binary frames without showing the stent struts (i.e., no stars are shown). The contours of the object shown in FIG. 23A corresponds to the contours of the object shown in FIG. 22A. Additionally, the contours of the object shown in FIG. 23C corresponds to the contours of the object shown in FIG. 22C. This is because, for example, the object shown in FIG. 22A and the object shown in FIG. 22C were both determined in step S2103 not to be below the threshold. Accordingly, based on a determination of No in step S2103, the flow proceeds to step S2105 and the object generated in step S2101 is used for the image frame corresponding to FIGS. 22A and 23A and, likewise, the object generated in step S2101 is used for the image frame corresponding to FIGS. 22C and 23C. FIG. 23B, in contrast, represents a recalculated object. For example, in step S2102, a feature of the object shown in FIG. 22B is compared to a threshold. In one or more embodiments, a feature of the object in FIG. 22B is determined to be below a threshold in step S2103. For example, due to missing or not detected struts in the binary frame of FIG. 22B, the binary object in FIG. 23B is recalculated using the pre and post objects. For example, the binary object in FIG. 22B is recalculated using the object shown in FIG. 23A and the object shown in FIG. 23C in order to generate the object shown in FIG. 23B. By interpolating the missing or not detected struts using the pre and post struts a realistic surface visualization of the stent is provided. In some embodiments, the computing system 101 averages missing struts of a frame using the pre and post frame struts and connects them using a spline. By interpolating the missing or not detected struts, the accuracy of the apposition percentage can be increased.

In the example, shown in FIGS. 22A-22C and FIGS. 23A-23C, the FIG. 22B may have been determined to be below the threshold because, for example, an area of the object in FIG. 22B may have been less than 90% of the area of the object shown in FIG. 22A. Accordingly, in one or more embodiments, the object shown in FIG. 22B may have been deleted and the computing system 101 may re-calculate this object by interpolating the points of the frame shown in FIG. 23A (or the corresponding frame shown in FIG. 22A) and the frame shown in FIG. 23C (or the corresponding frame shown in FIG. 22C) in order to generate the interpolated binary object shown in FIG. 23B. After generating all or a portion of the object by interpolation in step S2104, the flow proceeds to step S2105.

In step S2105, the computing system 101 determines whether another object is present that needs to be checked against a threshold, among the objects generated in step S2101. If another object is present (Yes in step S2105), the flow proceeds to step S2102. For example, a feature of the identified object is compared to a threshold. That is, steps S2102 and S2103 are performed for each object and, if the feature of the object is below the threshold, step S2104 is also performed. On the other hand, if the computing system 101 determines that no other object needs to be compared against a threshold (No in step S2105), the flow proceeds to S2106.

In step S2106, the computing system 101 translates contours of objects for a stent from two dimensions to three dimensions. In one or more embodiments, the computing system 101 generates a representation of a three dimensional shape of the endovascular device based on the one or more images identified in step S608 that correspond to the endovascular device. In some embodiments, the representation of the three dimensional shape of the endovascular device is generated using the respective objects corresponding to the one or more images that correspond to the endovascular device. For example, each of the objects generated in step S2101 and/or in step S2104 by interpolation are used to generate the three dimensional shape of the endovascular device by translating the contours of the objects.

In one or more embodiments, step S2106 includes translating a contour set, which corresponds to an endovascular device (e.g., stent), in the 3D space. The contours of the endovascular device binary objects are translated from the 2D space to the 3D. To translate the binary objects, M (M≠even) equidistant points of each of the binary contours are extracted clock wisely and a triangulation approach is implemented to construct the mesh surfaces of the 3D stent. The M contours points are connected and construct a triangle mesh and its volume.

In step S2107, the computing system 101 obtains lumen contour data for the image(s) that correspond to the stent. For example, in some embodiments, the computing system 101 obtains lumen contour data for at least the image(s) that correspond to the images identified in step S608 for the stent. The lumen border can be automatically or semi-automatically detected in the images using any suitable method.

In step S2108, the computing system 101 translates the lumen contour data from two dimensions to three dimensions. In one or more embodiments, the computing system 101 generates a representation of a three dimensional shape of a lumen segment based on the one or more images that correspond to the endovascular device. For example, the lumen segment may be a portion of the lumen contour data that corresponds to the image frames of the endovascular device. In some embodiments, step S2108 includes translating a contour set, which corresponds to the lumen contour data obtained in step S2107, in the 3D space. In one or more embodiments, the lumen segment contours of the corresponding frames (stented frames), provided by an independent algorithm, are translated to a 3D volume using the same procedure used in step S2106 for the stent contours. For example, the contours of the lumen border objects are translated from the 2D space to the 3D. To translate the lumen contours, M (M≠even) equidistant points of each of the lumen contours are extracted clock wisely and a triangulation approach is implemented to construct the mesh surfaces of the 3D lumen. The M contours points are connected and construct a triangle mesh and its volume.

In step S2109, the computing system 101 presents the representation of the three dimensional shape of the stent superimposed on the representation of three dimensional shape of the lumen. For example, in some embodiments, the computing system 101 generates the representation of a three dimensional shape of the endovascular device based on the one or more images identified in step S608 that correspond to the endovascular device. In one or more embodiments, the computing system presents the representation of the three dimensional shape of the endovascular device together with the representation of the three dimensional shape of the lumen segment such that the three dimensional shape of the endovascular device is superimposed on the three dimensional shape of the lumen segment. That is, the stent volume and the lumen segment volume are projected together in the three dimensional space.

Figure 24:
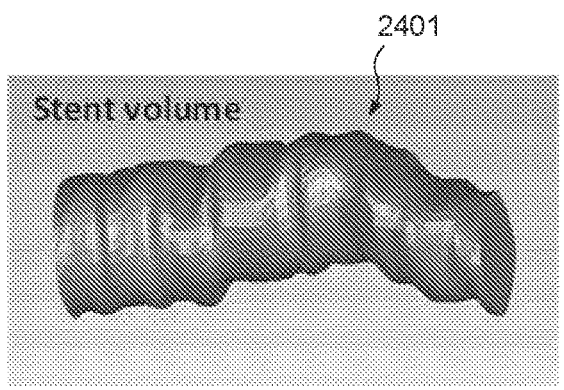
FIG. 24 illustrates an example representation of a 3D shape of a stent, which is representative of the stent volume.

FIG. 24 illustrates an example stent volume 2401. For example, the example stent volume 2401 is a representation of a three dimensional shape of the endovascular device generated based on the one or more images identified in step S608 that correspond to the endovascular device.

Figure 25:
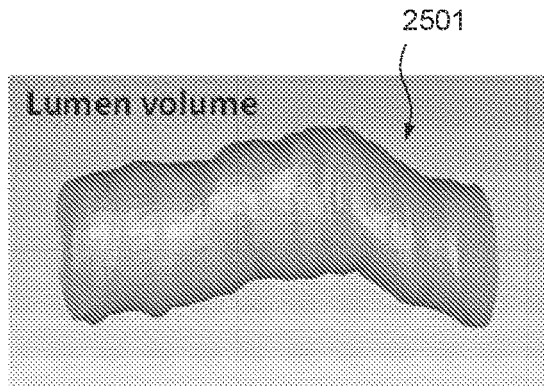
FIG. 25 illustrates an example representation of a 3D shape of a lumen, which is representative of the lumen volume.

FIG. 25 illustrates an example lumen volume 2501. For example, the example lumen volume 2501 is a representation of a three dimensional shape of the lumen segment generated based on the lumen contour data that corresponds to the image frames of the endovascular device.

Figure 26A:
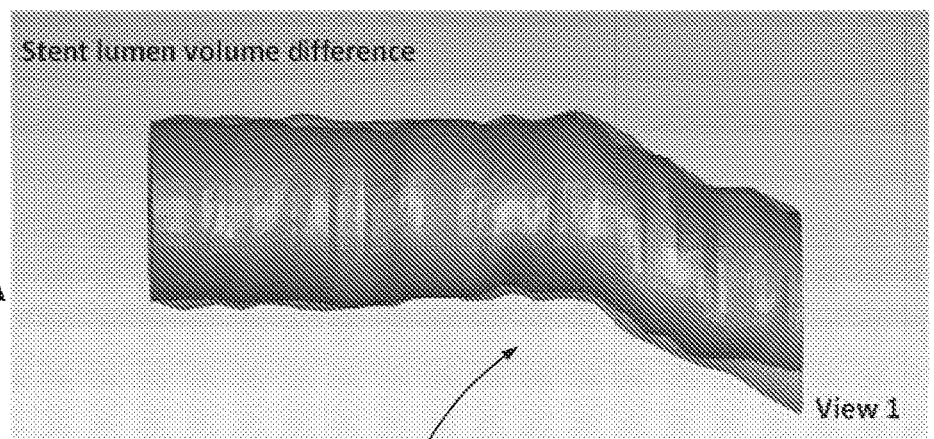
FIGS. 26A-26C illustrate three example views of a volume difference presented at different angles in FIG. 26A (View 1), FIG. 26B (View 2), and FIG. 26C (View 3), each depicting a difference between the lumen volume and the stent volume.
Figure 26B:
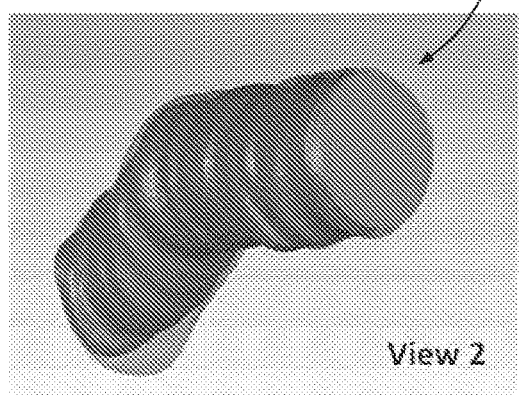
Figure 26C:
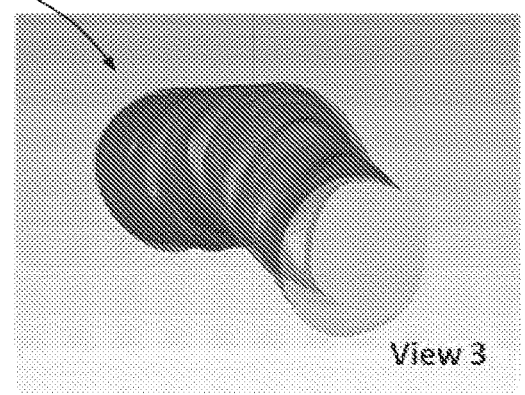

FIGS. 26A-26C illustrate three example views of the representation of the three dimensional shape of the stent superimposed on the representation of three dimensional shape of the lumen segment. In FIGS. 26A-26C, the three examples of a superimposed view 2601 illustrate a volume difference between the stent and the lumen segment presented at different angles at FIG. 26A (View 1), FIG. 26B (View 2), and FIG. 26C (View 3). According to one or more embodiments, by providing the three dimensional view of the stent within the three dimensional lumen segment, a better understanding of the malapposition (not fully apposed) of the stent is provided since the curvature of the artery is shown. The examples View 1, View 2, and View 3 are examples views, but the disclosure is not limited to the views shown in FIGS. 26A-26C. For example, the superimposed view 2601 may be presented on a display (for example, the display 111) and may be rotated or otherwise adjusted by a user providing inputs indicating how the view is to be manipulated.

In step S2110, the computing system 101 calculates and presents an apposition value of the stent relative to the vessel wall based on a volume difference between the three dimensional shape of lumen and the three dimensional shape of stent. In some embodiments, the computing system 101 determines an apposition value of the endovascular device relative to the vessel wall using a representation of a 3D shape of a lumen segment that corresponds to the endovascular device, the apposition value based on a volume difference between the 3D shape of the lumen segment and the 3D shape of the endovascular device. For example, in some embodiments, the stent 3D volume is subtracted from the lumen 3D volume to obtain a volume difference between the respective 3D volumes, and the stent apposition percentage is determined based on the volume difference. In one or more embodiments, information indicating the apposition value may be presented. In some embodiments, the information indicating the apposition value comprises an indication of a percentage of the endovascular device not fully apposed to the vessel wall. For example, the computing system 101 may calculate the two volumes and subtract the stent volume from the lumen volume to get the stent apposition percentage.

According to one or more embodiments, by performing three dimensional measurements in a device and structure that are truly represented in the three-dimensional space, a realistic percentage can be calculated. In addition, by depicting the results in the three dimensional space, a better understanding of the apposition phenomenon is provided to the user. Thus, by virtue of one or more embodiments, the computing system 101 calculates what percentage of the device is not fully apposed within the vessel. For example, the volume difference between the stent volume and the lumen segment volume defines the realistic apposition percentage of the stent. Accordingly, by calculating the stent apposition in the three-dimensional space, the apposition accuracy is increased. In one or more embodiments, the superimposed view of the volumes and the information indicating the apposition value are simultaneously presented. By providing such information simultaneously, a better understanding of the device apposition failure is provided.

Figure 27:
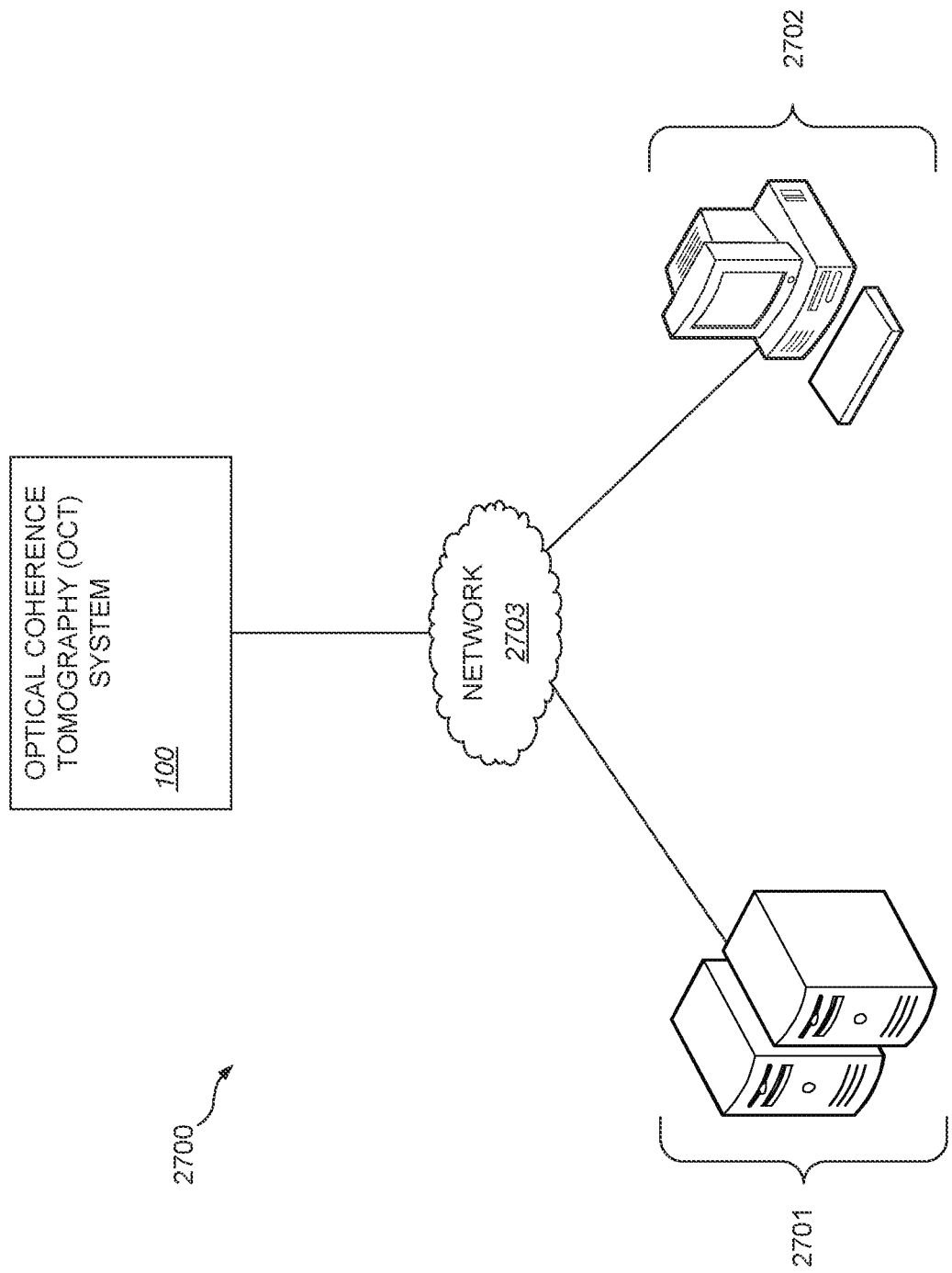
FIG. 27 illustrates an example network environment.

FIG. 27 depicts an example network environment 2700. The OCT system 100, a server computing system 2701, and a client computing system 2702 are connected to a network 2703. In some embodiments, the computing system 101 included in the OCT system 100 is connected to the network 2703. In some embodiments, one or more operations or functions described herein is performed by one or more of the OCT system 100, the server computing system 2701, and the client computing system 2702 connected to the network 2703. The network 2703 couples one or more servers and one or more clients to each other. The network 2703 may be any suitable network. For example, one or more portions of the network 2703 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. The network 2703 may include one or more networks.

According to some embodiments, one or more of the OCT system 100, the server computing system 2701, and the client computing system 2702 interact with one or more other entities on the network 2703. The OCT system 100, the server computing system 2701, and the client computing system 2702 may use any suitable protocol(s), standard(s), data exchange format(s), or combination(s) of these, to communicate with and send/receive information to/from one or more of the devices and computing systems described herein. In some embodiments, one or more of the OCT system 100, the server computing system 2701, and the client computing system 2702 include one or more programs, applications, GUIs, data, and other suitable resource(s) for performing one or more operations, functions, and/or processes described herein.

In some embodiments, the server computing system 2701 includes one or more servers or data stores for storing files (e.g., medical images), data, and/or application programs described herein. For example, image datasets including intravascular images generated by the OCT system 100 may be sent to the server computing system 2701. In some embodiments, the server computing system 2701 executes all or a part of one or more methods described herein. For example, the server computing system 2701 may obtain image data and perform one or more operations or processes using the image data. For example, the server computing system 2701 may detect a stent, artifact, and/or lumen edge, or may output stent apposition information in response to a request. The server computing system 2701 may include one or more application(s) servers, web servers, file servers, database servers, or other server. In some embodiments, the server computing system 2701 is unitary. In some embodiments, the server computing system 2701 is distributed. The server computing system 2701 may span multiple locations. The server computing system 2701 may span multiple machines (e.g., servers, mainframes, desktop computers, laptop computers).

In some embodiments, the client computing system 2702 includes one or more computing devices (e.g., desktop computers, laptop computers, smartphones, tablet computers) executing a browser and/or application(s) for accessing resources on the network 2703. The client computing system 2702 may obtain files (e.g., medical images) from the OCT system 100, or the server computing system 2701, and may process images. For example, the client computing system 2702 may detect a stent, artifact, and/or lumen edge, or may output stent apposition information. In some embodiments, the client computing system 2702 executes all or a part of one or more methods described herein.

Figure 28:
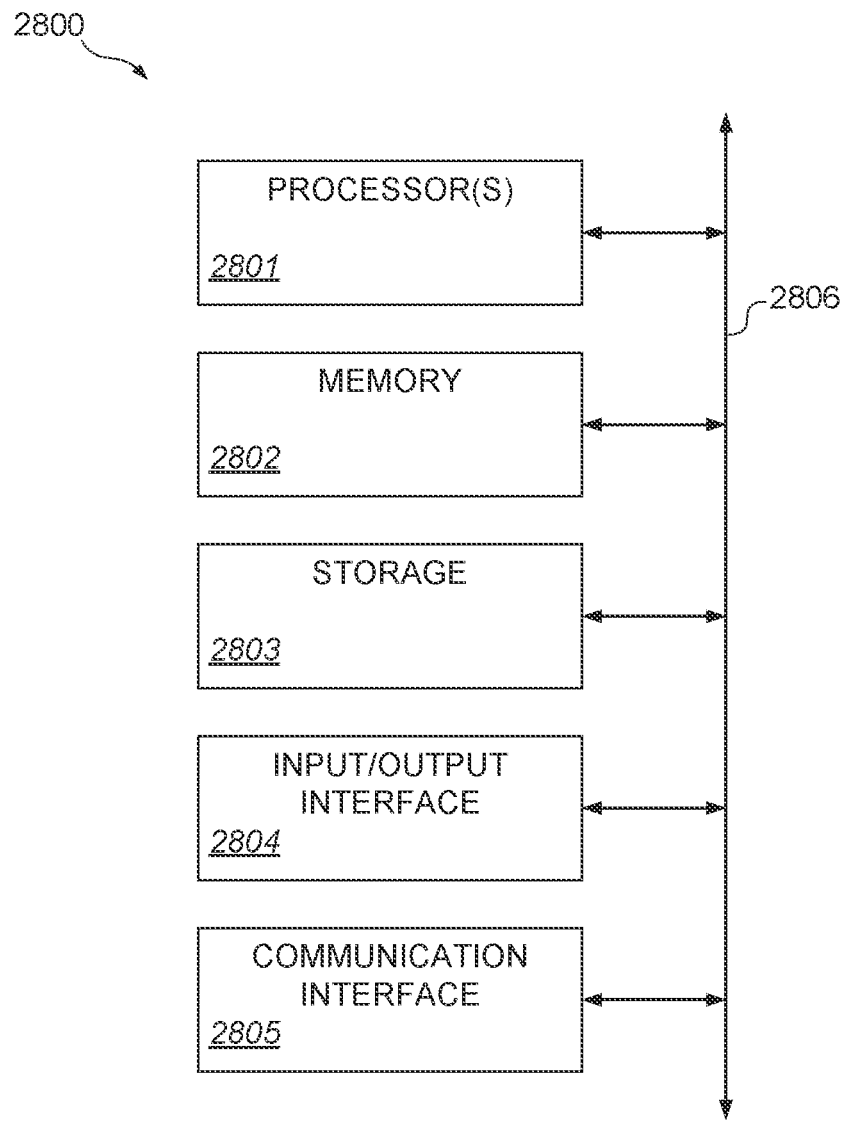
FIG. 28 illustrates an example computing system.

FIG. 28 illustrates an example computing system 2800. According to various embodiments, all or a portion of the description of the computing system 2800 is applicable to all or a portion of one or more of the computing system 101, the server computing system 2701, the client computing system 2702, and the OCT system 100. In some embodiments, the computing system 101 comprises the computing system 2800. In some embodiments, the computing system 2800 provides functionality described herein. In some embodiments, software running on the computing system 2800 performs one or more operations described herein.

The term computing system as used herein includes but is not limited to one or more software modules, one or more hardware modules, one or more firmware modules, or combinations thereof, that work together to perform operations on electronic data. The physical layout of the modules may vary. A computing system may include multiple computing devices coupled via a network. A computing system may include a single computing device where internal modules (such as a memory and processor) work together to perform operations on electronic data. Also, the term resource as used herein includes but is not limited to an object that can be processed at a computing system. A resource can be a portion of executable instructions or data.

In some embodiments, the computing system 2800 performs one or more steps of one or more methods described or illustrated herein. In some embodiments, the computing system 2800 provides functionality described or illustrated herein. In some embodiments, software running on the computing system 2800 performs one or more steps of one or more methods described or illustrated herein or provides functionality described or illustrated herein. Some embodiments include one or more portions of the computing system 2800.

The computing system 2800 includes one or more processor(s) 2801, memory 2802, storage 2803, an input/output (I/O) interface 2804, a communication interface 2805, and a bus 2806. The computing system 2800 may take any suitable physical form. By way of example, the computing system 2800 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, PDA, a server, a tablet computer system, or a combination of two or more of these.

The processor(s) 2801 include hardware for executing instructions, such as those making up a computer program. The processor(s) 2801 may retrieve the instructions from the memory 2802, the storage 2803, an internal register, or an internal cache. The processor(s) 2801 then decode and execute the instructions. Then, the processor(s) 2801 write one or more results to the memory 2802, the storage 2803, the internal register, or the internal cache. The processor(s) 2801 may provide the processing capability to execute the operating system, programs, user and application interfaces, and any other functions of the computing system 2800.

The processor(s) 2801 may include a central processing unit (CPU), one or more general-purpose microprocessor(s), application-specific microprocessor(s), and/or special purpose microprocessor(s), or some combination of such processing components. The processor(s) 2801 may include one or more graphics processors, video processors, audio processors and/or related chip sets.

In some embodiments, the memory 2802 includes main memory for storing instructions for the processor(s) 2801 to execute or data for the processor(s) 2801 to operate on. By way of example, the computing system 2800 may load instructions from the storage 2803 or another source to the memory 2802. During or after execution of the instructions, the processor(s) 2801 may write one or more results (which may be intermediate or final results) to the memory 2802. One or more memory buses (which may each include an address bus and a data bus) may couple the processor(s) 2801 to the memory 2802. One or more memory management units (MMUs) may reside between the processor(s) 2801 and the memory 2802 and facilitate accesses to the memory 2802 requested by the processor(s) 2801. The memory 2802 may include one or more memories. The memory 2802 may be random access memory (RAM).

The storage 2803 stores data and/or instructions. As an example and not by way of limitation, the storage 2803 may include a hard disk drive, a floppy disk drive, flash memory, an optical disc, a magneto-optical disc, magnetic tape, or a Universal Serial Bus (USB) drive or a combination of two or more of these. In some embodiments, the storage 2803 is a removable medium. In some embodiments, the storage 2803 is a fixed medium. In some embodiments, the storage 2803 is internal to the computing system 2800. In some embodiments, the storage 2803 is external to the computing system 2800. In some embodiments, the storage 2803 is nonvolatile, solid-state memory. In some embodiments, the storage 2803 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. The storage 2803 may include one or more memory devices. One or more program modules stored in the storage 2803 may be configured to cause various operations and processes described herein to be executed. The storage 2803 may store application data, program modules and other information. In some embodiments, the application(s) 112 reside on the storage 2803 and execute on the computing system 2800. In some embodiments, the data store 113 resides on the storage 2803. One or more program modules stored in the storage 2803 are configured to cause various operations and processes described herein to be executed. For example, programs of the application(s) 112 may include instructions that, when executed by one or more processors, cause the one or more processors to perform one or more operations described with respect to one or more of FIG. 6, FIG. 10, FIG. 14, FIG. 21, and FIG. 29.

The I/O interface 2804 includes hardware, software, or both providing one or more interfaces for communication between the computing system 2800 and one or more I/O devices. The computing system 2800 may include one or more of these I/O devices, where appropriate. One or more of these I/O devices may enable communication between a person and the computing system 2800. As an example and not by way of limitation, an I/O device may include a light source, a keyboard, keypad, microphone, monitor, mouse, speaker, still camera, stylus, tablet, touch screen, trackball, video camera, another suitable I/O device or a combination of two or more of these. An I/O device may include one or more sensors. In some embodiments, the I/O interface 2804 includes one or more device or software drivers enabling the processor(s) 2801 to drive one or more of these I/O devices. The I/O interface 2804 may include one or more I/O interfaces.

The communication interface 2805 includes hardware, software, or both providing one or more interfaces for communication (such as, for example, packet-based communication) between the computing system 2800 and one or more other computing systems or one or more networks. As an example and not by way of limitation, the communication interface 2805 may include a network interface card (NIC) or a network controller for communicating with an Ethernet or other wire-based network or a wireless NIC (WNIC) or wireless adapter for communicating with a wireless network, such as a WI-FI network. This disclosure contemplates any suitable network and any suitable communication interface 2805 for it. As an example and not by way of limitation, the computing system 2800 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the computing system 2800 may communicate with a wireless PAN (WPAN) (such as, for example, a Bluetooth WPAN or an ultra wideband (UWB) network), a WI-FI network, a WI-MAX network, a cellular telephone network (such as, for example, a Global System for Mobile Communications (GSM) network), or other suitable wireless network or a combination of two or more of these. The computing system 2800 may include any suitable communication interface 2805 for any of these networks, where appropriate. The communication interface 2805 may include one or more communication interfaces 2805.

The bus 2806 interconnects various components of the computing system 2800 thereby enabling the transmission of data and execution of various processes. The bus 2806 may include one or more types of bus structures including a memory bus or memory controller, a peripheral bus, and a local bus using any of a variety of bus architectures.

Figure 29:
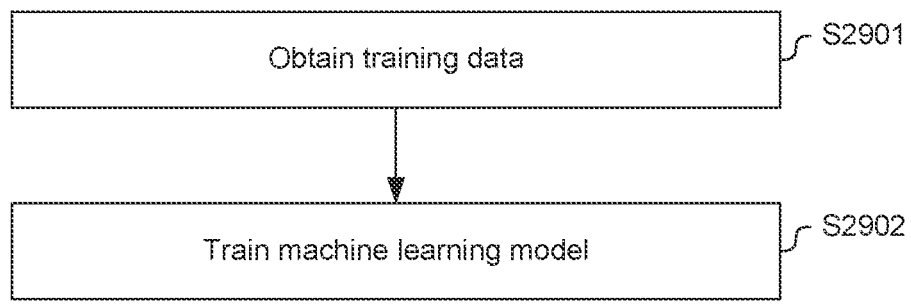
FIG. 29 illustrates an example operational flow for training a machine-learning model.

FIG. 29 illustrates an example operational flow for training a machine-learning model. In some embodiments, one or more of the steps of FIG. 29 are performed at the computing system 2800 by executing program instructions of the application(s) 112 on the computing system 2800.

In step S2901, the computing system 2800 obtains training data for training a machine learning model. The training data includes multiple training examples including feature data corresponding to signal segments. In some embodiments, step S2901 includes obtaining the training data shown in FIG. 30.

Figure 30:
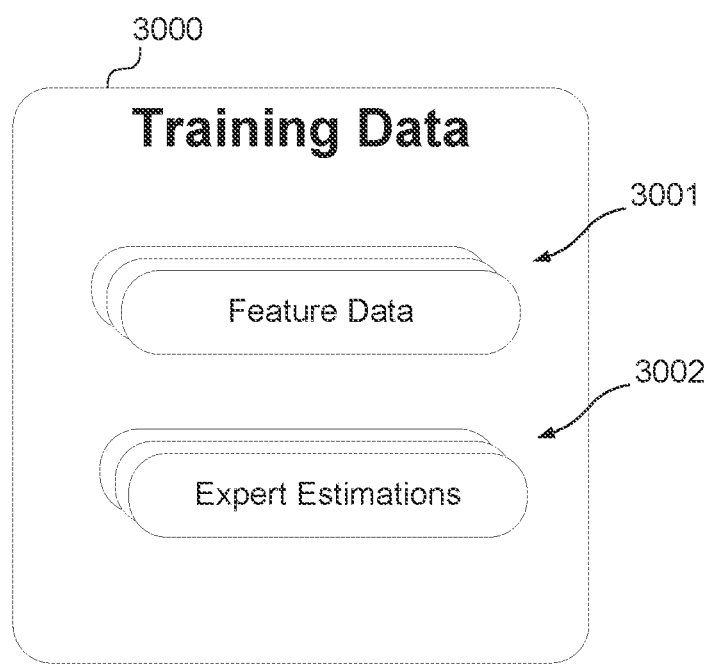
FIG. 30 illustrates example training data for training a machine-learning model.

FIG. 30 illustrates example training data 3000 for training a machine-learning model. According to one or more embodiments, the training data 3000 includes feature data 3001 and expert estimations 3002.

In one or more embodiments, the feature data 3001 includes signal segment feature data for a plurality of signal segments. In one or more embodiments, the feature data 3001 includes a low-state level and a high-state level for each signal segment. For example, in some embodiments, the feature data 3001 includes, for each signal segment, the low-state level and the high-state level in the bi-level waveform of the signal segment using the histogram method. In one or more embodiments, the feature data 3001 includes, for each signal segment, a signal-to-noise ratio between the signal segment and its moving average smoothed signal. The feature data 3001 may include any suitable feature data associated with a signal segment.

In one or more embodiments, the training data 3000 includes expert estimations 3002. For example, according to one or more embodiments, the training data 3000 includes signal segment feature data 3001 selected by one or more experts or supervisors to include a balanced dataset of stented segments and non-stented segments derived from many OCT pullback sequences. In some embodiments, feature data 3001 for signal segments are specified as stented segments or not stented segments using expert's estimations 3002. In some embodiments, the expert estimations 3002 include one or more labels related to, for example, a classification of a signal segment and/or a feature of a signal segment.

In one or more embodiments, step S2901 includes inputting the training data 3000 into a machine learning model. In some embodiments, the machine learning model is a classifier. For example, the machine learning model may be a Support Vector Machine (SVM) classifier.

In step S2902, the computing system 2800 trains the machine learning model. For example, the computing system 2800 may train the machine learning model using the training data obtained in step S2901. In some embodiments, the machine learning model is trained based on the training data 3000 of FIG. 30. In some embodiments, step S2902 includes training the machine learning model such that the machine learning model is a classifier.

In one or more embodiments, the machine learning model is trained, in step S2902, to classify a signal segment as either representative of image data of the endovascular device or, alternatively, not representative of image data of the endovascular device based on one or more signal features of the signal segment. In some embodiments, the machine learning model is trained to classify each signal segment based on one or more of the following signal features: the low-state level and high-state level in the bi-level waveform of the signal segment using the histogram method and the signal-to-noise ratio between the signal segment and its moving average smoothed signal.

According to one or more embodiments, to train the machine learning model, signal segments (for example, the 10-value signal segments 902 of FIG. 9 corresponding to 10 frames) are classified as stented or not using expert's estimations and a balanced dataset of the segments' features derived from at least seven stented arteries is created. In some embodiments, the machine learning model is trained to output a classification for each of the signal segments as either stent segment or not stent segment.

The above description serves to explain principles of the disclosure; but the disclosure should not be limited to the examples described above. For example, the order and/or timing of some of the various operations may vary from the examples given above without departing from the scope of the disclosure. Further by way of example, the type of network and/or computing systems may vary from the examples given above without departing from the scope of the disclosure. Other variations from the examples given above may also exist without departing from the scope of the disclosure. For example, various features of the illustrated examples could be modified, rearranged, or removed, or one or more features could be added without departing from the scope of the disclosure.

The scope of the present disclosure includes a computer-readable medium storing instructions that, when executed by one or more processors, cause the one or more processors to perform one or more embodiments of the disclosure described herein. Examples of a computer-readable medium include a hard disk, a floppy disk, a magneto-optical disk (MO), a compact-disk read-only memory (CD-ROM), a compact disk recordable (CD-R), a CD-Rewritable (CD-RW), a digital versatile disk ROM (DVD-ROM), a DVD-RAM, a DVD-RW, a DVD+RW, magnetic tape, a nonvolatile memory card, and a ROM. Computer-executable instructions can also be supplied to the computer-readable storage medium by being downloaded via a network.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure.

The scope of the following claims is to be accorded the broadest interpretation so as to encompass all such modifications and equivalent structures and functions.

What is claimed is:

1. A system comprising:
one or more processors; and
one or more non-transitory computer-readable media storing executable instructions configured to be executed by the one or more processors, wherein the one or more non-transitory computer-readable media and the one or more processors are configured to cause the system to:
obtain intravascular image data of a vessel wall and an endovascular device, the intravascular image data comprising a plurality of images;
generate a signal that represents the plurality of images;
identify, in the plurality of images, one or more images that correspond to the endovascular device based on the signal that represents the plurality of images;
generate a representation of a three-dimensional (3D) shape of the endovascular device based on the one or more images that correspond to the endovascular device;
determine an apposition value of the endovascular device relative to the vessel wall using a representation of a 3D shape of a lumen segment that corresponds to the endovascular device, the apposition value based on a volume difference between the 3D shape of the lumen segment and the 3D shape of the endovascular device; and
present information indicating the apposition value.

2. The system of claim 1, wherein each of the plurality of images is a cross-sectional image of the vessel, and wherein each of the one or more images that correspond to the endovascular device corresponds to a respective cross section of the endovascular device.

3. The system of claim 1, wherein each of the plurality of images corresponds to a respective group of A-lines, and wherein, to generate the signal that represents the plurality of images, the one or more non-transitory computer-readable media and the one or more processors are further configured to cause the system to:
generate a respective signal value for each of the plurality of images based on the respective group of A-lines corresponding to each of the plurality of images.

4. The system of claim 1, wherein the one or more non-transitory computer-readable media and the one or more processors are further configured to cause the system to:
divide the signal that represents the plurality of images into segments, wherein each of the signal segments corresponds to two or more sequential images of the plurality of images; and
input data of each signal segment into a classifier, which outputs a classification for each of the signal segments as either representative of image data of the endovascular device or, alternatively, not representative of image data of the endovascular device.

5. The system of claim 4, wherein, to identify the one or more images that correspond to the endovascular device, the one or more non-transitory computer-readable media and the one or more processors are further configured to cause the system to:
based on a classification of one or more signal segments as representative of image data of the endovascular device, identify one or more images corresponding to the one or more signal segments as the one or more images that correspond to the endovascular device.

6. The system of claim 4, wherein the classifier is a Support Vector Machine classifier.

7. The system of claim 4, wherein the classifier is a trained classifier and the classification for each of the signal segments is based on one or more signal features.

8. The system of claim 7, wherein the classification for each of the signal segments is based on a low-state level and a high-state level of each signal segment, and a signal-to-noise ratio between each signal segment and a moving average smoothed signal for the signal segment.

9. The system of claim 1, wherein the one or more non-transitory computer-readable media and the one or more processors are further configured to cause the system to:
using a two-dimensional representation of the intravascular image data, generate a binary mask that includes a representation of a guidewire; and
detect the guidewire in an image that corresponds to the endovascular device based on the binary mask, and exclude or remove the guidewire from the image.

10. The system of claim 1, wherein the one or more non-transitory computer-readable media and the one or more processors are further configured to cause the system to:
for each of the one or more images that correspond to the endovascular device:
generate an A-line signal by averaging A-lines of an A-line image;
detect strut candidates of an endovascular device at respective A-line signal valleys;
calculate a valley threshold as a mean value of the A-line signal divided by two; and
detect one or more struts based on a determination that each of the one or more struts corresponds to a respective A-line signal valley that is less than the valley threshold and does not belong to a guidewire pixel.

11. The system of claim 1, wherein the one or more non-transitory computer-readable media and the one or more processors are further configured to cause the system to:
detect, for each of the one or more images that correspond to the endovascular device, respective one or more struts of the endovascular device; and
generate a respective object for each of the one or more images that correspond to the endovascular device, each object representing a respective surface segment of the endovascular device, wherein the representation of the 3D shape of the endovascular device is generated using the respective objects corresponding to the one or more images that correspond to the endovascular device.

12. The system of claim 11, wherein, to generate a respective object for each of the one or more images that correspond to the endovascular device, the one or more non-transitory computer-readable media and the one or more processors are further configured to cause the system to:
generate a plurality of objects by applying a respective spline over the respective one or more struts for each of the plurality of the objects, wherein the plurality of the objects represent successive surface segments of the endovascular device.

13. The system of claim 11, wherein, to generate a respective object for each of the one or more images that correspond to the endovascular device, the one or more non-transitory computer-readable media and the one or more processors are further configured to cause the system to:
generate a first object by interpolating one or more portions of the first object using data of a second object representing a preceding surface segment of the endovascular device relative to the first object, or using data of a third object representing a succeeding surface segment of the endovascular device relative to the first object, or using both the data of the second object and the data of the third object.

14. The system of claim 13, wherein, to generate the first object, the one or more non-transitory computer-readable media and the one or more processors are further configured to cause the system to:
compare a size of the first object to a threshold; and
generate the first object by interpolating one or more missing struts of the first object using one or more struts of the second object and one or more struts of the third object when the size of the first object is below the threshold.

15. The system of claim 1, wherein the one or more non-transitory computer-readable media and the one or more processors are further configured to cause the system to:
present the representation of the 3D shape of the endovascular device together with the representation of the 3D shape of the lumen segment such that the 3D shape of the endovascular device is superimposed on the 3D shape of the lumen segment.

16. The system of claim 1, wherein the representation of the 3D shape of the lumen segment is generated based on the one or more images that correspond to the endovascular device.

17. The system of claim 1, wherein the information indicating the apposition value comprises an indication of a percentage of the endovascular device not fully apposed to the vessel wall.

18. The system of claim 1, wherein the endovascular device is a stent, and wherein the intravascular image data includes image data of the stent disposed within a lumen of the vessel.

19. A method comprising:
obtaining intravascular image data of a vessel wall and an endovascular device, the intravascular image data comprising a plurality of images;
generating a signal that represents the plurality of images;
identifying, in the plurality of images, one or more images that correspond to the endovascular device based on the signal that represents the plurality of images;
generating a representation of a three-dimensional (3D) shape of the endovascular device based on the one or more images that correspond to the endovascular device;
determining an apposition value of the endovascular device relative to the vessel wall using a representation of a 3D shape of a lumen segment that corresponds to the endovascular device, the apposition value based on a volume difference between the 3D shape of the lumen segment and the 3D shape of the endovascular device; and
presenting information indicating the apposition value.

20. One or more non-transitory computer-readable storage media storing instructions, which when executed by one or more computing devices, cause the one or more computing devices to perform operations comprising:
obtaining intravascular image data of a vessel wall and an endovascular device, the intravascular image data comprising a plurality of images;
generating a signal that represents the plurality of images;
identifying, in the plurality of images, one or more images that correspond to the endovascular device based on the signal that represents the plurality of images;
generating a representation of a three-dimensional (3D) shape of the endovascular device based on the one or more images that correspond to the endovascular device;
determining an apposition value of the endovascular device relative to the vessel wall using a representation of a 3D shape of a lumen segment that corresponds to the endovascular device, the apposition value based on a volume difference between the 3D shape of the lumen segment and the 3D shape of the endovascular device; and
presenting information indicating the apposition value.

* * * * *